US010769790B2

(12) United States Patent
Khalil et al.

(10) Patent No.: US 10,769,790 B2
(45) Date of Patent: Sep. 8, 2020

(54) METHODS OF CANCER DETECTION

(71) Applicant: University of Maine System Board of Trustees, Orono, ME (US)

(72) Inventors: Andre Khalil, Orono, ME (US); Kendra Ann Batchelder, Bangor, ME (US)

(73) Assignee: UNIVERSITY OF MAINE SYSTEM BOARD OF TRUSTEES, Orono, ME (US)

( * ) Notice: Subject to any disclaimer, the term of this patent is extended or adjusted under 35 U.S.C. 154(b) by 0 days.

(21) Appl. No.: 16/577,238

(22) Filed: Sep. 20, 2019

(65) Prior Publication Data
US 2020/0082532 A1 Mar. 12, 2020

Related U.S. Application Data

(62) Division of application No. 14/786,366, filed as application No. PCT/US2014/035153 on Apr. 23, 2014, now Pat. No. 10,467,755.

(60) Provisional application No. 61/815,209, filed on Apr. 23, 2013.

(51) Int. Cl.
G06T 7/00 (2017.01)
G06T 7/48 (2017.01)
A61B 5/00 (2006.01)
A61B 6/00 (2006.01)
A61B 5/08 (2006.01)
A61B 5/20 (2006.01)

(52) U.S. Cl.
CPC ............ *G06T 7/0016* (2013.01); *A61B 5/726* (2013.01); *A61B 5/7257* (2013.01); *A61B 6/502* (2013.01); *G06T 7/48* (2017.01); *A61B 5/08* (2013.01); *A61B 5/201* (2013.01); *A61B 5/4064* (2013.01); *A61B 5/425* (2013.01); *A61B 5/4244* (2013.01); *A61B 5/4325* (2013.01); *A61B 5/444* (2013.01); *A61B 2576/00* (2013.01); *G06T 2207/20021* (2013.01); *G06T 2207/20064* (2013.01); *G06T 2207/30024* (2013.01)

(58) Field of Classification Search
CPC G06T 7/0012; G06T 7/40; G06T 7/41; G06T 7/48; G06T 2207/30024; G06T 2207/30096; A61B 6/5217; A61B 8/5223; A61B 2567/00
See application file for complete search history.

(56) References Cited

U.S. PATENT DOCUMENTS

| | | | |
|---|---|---|---|
| 7,058,210 B2 | 6/2006 | Mundy et al. | 382/128 |
| 7,761,240 B2 | 7/2010 | Saidi et al. | 702/19 |
| 10,467,755 B2 | 11/2019 | Khalil et al. | G06T 7/0016 |
| 2004/0151358 A1 | 8/2004 | Yanagita et al. | 382/132 |
| 2004/0259144 A1 | 12/2004 | Prabhu | 435/6 |
| 2006/0064248 A1* | 3/2006 | Saidi et al. | G06K 9/0014 702/19 |
| 2010/0177950 A1* | 7/2010 | Donovan et al. | G16H 50/30 382/133 |
| 2011/0182494 A1* | 7/2011 | Sokolov et al. | B82Y 35/00 382/133 |
| 2013/0066199 A1* | 3/2013 | Ramanujan | A61B 5/0071 600/431 |
| 2013/0096438 A1* | 4/2013 | Fehre et al. | A61B 1/041 600/478 |
| 2014/0233826 A1* | 8/2014 | Agaian et al. | G06K 9/46 382/133 |
| 2016/0055636 A1 | 2/2016 | Khalil et al. | G06T 7/0016 |

FOREIGN PATENT DOCUMENTS

| | | | |
|---|---|---|---|
| CN | 101727537 A | 6/2010 | G06F 19/00 |
| WO | WO-99/44010 A1 | 9/1999 | |
| WO | WO-2008/035286 A2 | 3/2008 | |
| WO | WO-2011/008262 A2 | 1/2011 | G01N 33/483 |
| WO | WO-2011/130645 A1 | 10/2011 | G01N 33/48 |

OTHER PUBLICATIONS

Hamilton, E. K. et al., Diagnostic Classification of Digital Mammograms by Wavelet-Based Spectral Tools: A Comparative Study, IEEE International Conference on Bioinformatics and Biomedicine, 384-389 (2011).
International Search Report of PCT/US14/35153, 3 pages (dated Oct. 1, 2014).
Kestener et al., Wavelet-based multifractral formalism to assist in diagnosis in digitized mammograms, Imaga Anal. Sterol., 20: 169-179 (2001).
Kestener, P., Analyse multifractale 2D et 3D à l'aide de la transformation en ondelettes: application en mammographie et en tubulence développée, Interface homme-machine [cs.HC]. Université Sciences et Technologies—Bordeaux I, 2003. Français. Retrieved from Internet:URL:https://pdfs.semanticscholar.org/9933/b69bee5b73d98e41517d373d5b4ffa4c1797.pdf?_ga=2.55538147.935467161.1559641028-90525902.1550067972. Accessed on Jun. 4, 2019. [French].

(Continued)

Primary Examiner — Andrew W Johns
(74) Attorney, Agent, or Firm — Choate, Hall & Stewart LLP; Brian E. Reese; Samuel R. Polio

(57) ABSTRACT

The present invention provides, among other things, methods of identifying cancerous or pre-cancerous tissue including providing a first region of tissue from a subject, calculating a roughness exponent for the first region of tissue, and comparing the roughness exponent of the first region of tissue to 0.5, wherein a difference of less than 0.2 between the roughness exponent of the first region of tissue and 0.5 indicates that the tissue is cancerous or pre-cancerous. Additionally, the present invention provides methods including providing a first view of a region of tissue, providing a second view of a region of tissue, calculating a first fractal dimension for the first view of the region of tissue, and calculating a second fractal dimension for the second view of the region of tissue, wherein if the fractal dimension of at least one of the first fractal dimension and the second fractal dimension is in the fractal zone, the region of tissue is considered cancerous. Also provided are systems for performing these assessments.

13 Claims, 14 Drawing Sheets

(56) References Cited

OTHER PUBLICATIONS

Lopes, R. et al., Prostate cancer characterization on MR images using fractal features, Med. Phys. 38(1): 83-95 (2011).
Richard, F. and Bierme, H, Statistical tests of Anisotropy for Fractional Brownian Textures. Application to Full-Field Digital Mammography, Journal of Mathematical Imaging and Vision, 36(3): 227-240 (2010).
Written Opinion of PCT/US14/35153, 14 pages (dated Oct. 1, 2014).

* cited by examiner

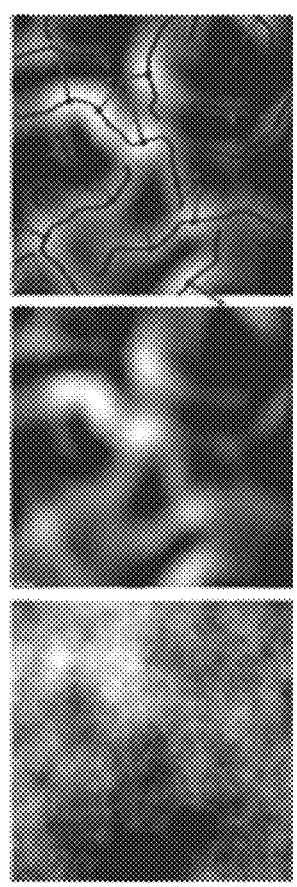
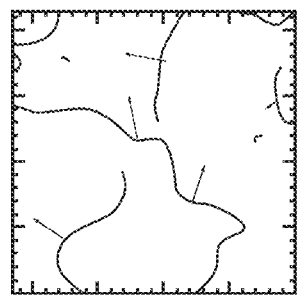
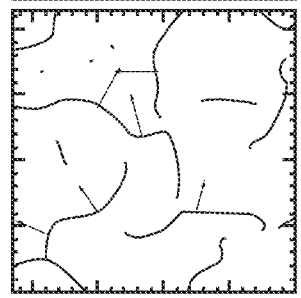
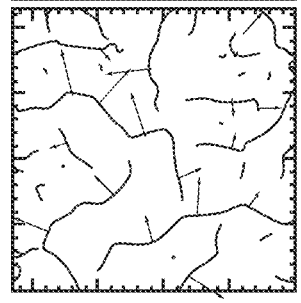
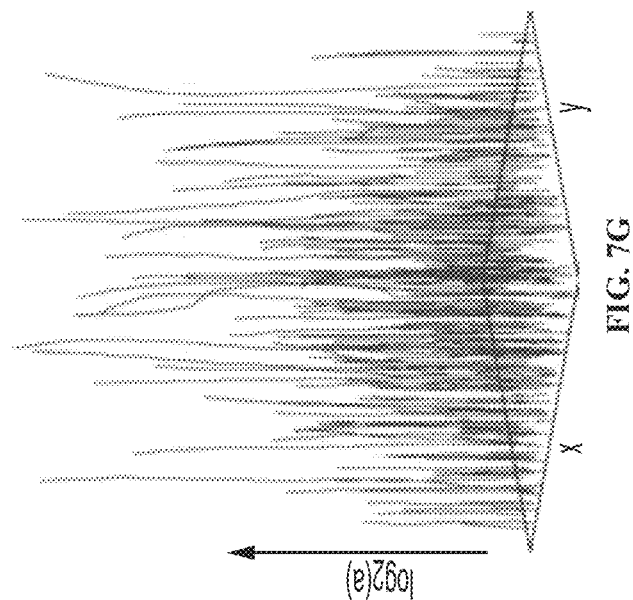

METHODS OF CANCER DETECTION

CROSS-REFERENCE TO RELATED APPLICATIONS

This patent application is a divisional application of U.S. application Ser. No. 14/786,366, filed Oct. 22, 2015, now issued U.S. Pat. No. 10,467,755, which was a U.S. National Stage Entry of International Patent Application No. PCT/US2014/035153, filed Apr. 23, 2014, which claims priority to U.S. Provisional Application No. 61/815,209, filed Apr. 23, 2013, the contents of each of which are hereby incorporated by reference in their entirety for all purposes herein.

BACKGROUND

The human body is composed of about ten trillion cells, and throughout a lifetime cells go through many damaging processes that concern their genetic programming. However, not all of these mutations result in cancer. As it turns out, many individuals actually have occult tumors throughout their bodies that are only discovered through microscopic investigation during autopsy. Therefore, there must be some mechanism that prohibits the growth and development of tumors.

Recent research has pointed to the microenvironment of potential tumors to help suppress malignant phenotype and instruct otherwise malignant cells to participate in normal development. The microenvironment may actually provide tumor suppressive signals as long as the tissue architecture is controlled, but as the structure of healthy tissue is lost, the tissue has the potential to become a tumor promoter. Thus, considering the tissue surrounding the tumor, along with the lesion, may be important in identifying potential cancerous tissue.

SUMMARY OF THE INVENTION

The present invention is based, in part, on the realization that disorder of the microenvironment surrounding a portion of tissue in a subject may be indicative of the presence of, or pre-disposition toward developing, cancer in that tissue. Among other things, the present invention provides, for the first time, methods for analyzing the amount and distribution of disorder across tissue in order to predict the presence of, or propensity of tissue to develop, cancer. In some embodiments, provided methods include analysis of images of target tissue, as opposed to analysis of the tissue itself In some embodiments, provided methods include analysis of tissue or images of tissue adjacent to a target tissue/tissue region of interest, as opposed to the target tissue itself.

The present invention provides, among other things, methods of identifying cancerous or pre-cancerous tissue including providing a first region of tissue from a subject, calculating a roughness exponent (e.g., a Hurst exponent) for the first region of tissue, and comparing the roughness exponent of the first region of tissue to 0.5, wherein a difference of less than 0.2 between the roughness exponent of the first region of tissue and 0.5 indicates that the tissue is cancerous or pre-cancerous. In some embodiments, the providing, calculating, and comparing steps are each performed a plurality of times. In some embodiments, the plurality of times is at least 10, at least 100, or at least 1,000. In some embodiments, performing the providing, calculating and comparing steps a plurality of times allows for a higher resolution characterization of the morphology of the tissue surrounding a region of tissue suspected to be cancerous or pre-cancerous.

In some embodiments, the difference between the roughness exponent values and 0.5 may be less than 0.2. In some embodiments, the difference between the roughness exponent of the first region of tissue and 0.5 is less than or equal to 0.15. In some embodiments, the difference between the roughness exponent of the first region of tissue and 0.5 is less than or equal to 0.1. In some embodiments, the difference between the roughness exponent of the first region of tissue and 0.5 is less than or equal to 0.05.

In some embodiments, a roughness exponent is calculated from one or more images of a target tissue. In some embodiments, a roughness exponent is calculated from two or more images of a first region of tissue. In some embodiments, each of the two or more images are taken from different angles and/or points of view. In some embodiments, a roughness exponent is calculated for two or more regions of tissue. In some embodiments, the two or more regions of tissue are from a single organ. In some embodiments, the two or more regions of tissue are from different organs.

A roughness exponent may be generated via any appropriate multi-scale analytical method. In some embodiments, the roughness exponent is calculated using one or more multi-scale methods selected from a wavelet-transform modulus maxima, a wavelet leader, detrended fluctuation, and Fourier analysis. A roughness exponent may also be calculated using any mathematically related and/or similar multi-scale density fluctuation assessment method yielding an exponent or spectrum of exponents that is similar and/or can complement the use of the Hurst exponent. In some embodiments, a roughness exponent is calculated from two-dimensional data. In some embodiments, a roughness exponent is calculated from three dimensional data (e.g., 3D data cubes).

In some embodiments, the present invention additionally provides methods including providing a first view of a region of tissue; providing a second view of the region of tissue; calculating a first fractal dimension for the first view of the region of tissue; and calculating a second fractal dimension for the second view of the region of tissue; wherein if the fractal dimension of at least one of the first fractal dimension and the second fractal dimension is in the fractal zone, the region of tissue is considered cancerous. In some embodiments, provided methods further comprise treating the region of tissue if it is cancerous.

In some embodiments, the fractal zone is defined as a polygon consisting of a central square and a first, second, third, and fourth extending triangular region as plotted on a graph of the fractal dimension of the first view of the region of tissue by the fractal dimension of the second view of the region of tissue.

In some embodiments, the central square and first, second, third and fourth extending triangular regions are defined by the following fractal dimensions, as plotted on a graph of the fractal dimension of the first view by the fractal dimension of the second view:

central square: (1.2, 1.2), (1.2, 1.8), (1.8, 1.2)(1.8, 1.8);
first extending triangular region: (0.5, 1.5), (1.2, 1.2), (1.2, 1.8);
second extending triangular region: (1.5, 0.5), (1.2, 1.2), (1.8, 1.2);
third extending triangular region: (1.5, 2.3), (1.2, 1.8), (1.8, 1.8); and fourth extending triangular region: (2.3, 1.5), (1.8, 1.2), (1.8, 1.8).

In some embodiments, the central square and first, second, third and fourth extending triangular regions are defined by the following fractal dimensions, as plotted on a graph of the fractal dimension of the first view by the fractal dimension of the second view:

central square: (1.1, 1.1), (1.1, 1.9), (1.9, 1.1)(1.9, 1.9);
first extending triangular region: (0.5, 1.5), (1.1, 1.1), (1.1, 1.9);
second extending triangular region: (1.5, 0.5), (1.1, 1.1), (1.9, 1.1);
third extending triangular region: (1.5, 2.3), (1.1, 1.9), (1.9, 1.9); and
fourth extending triangular region: (2.3, 1.5), (1.9, 1.1), (1.9, 1.9).

In some embodiments, the central square and first, second, third and fourth extending triangular regions are defined by the following fractal dimensions, as plotted on a graph of the fractal dimension of the first view by the fractal dimension of the second view:

central square: (1.3, 1.3), (1.3, 1.7), (1.7, 1.3)(1.7, 1.7);
first extending triangular region: (0.5, 1.5), (1.3, 1.3), (1.3, 1.7);
second extending triangular region: (1.5, 0.5), (1.3, 1.3), (1.7, 1.3);
third extending triangular region: (1.5, 2.3), (1.3, 1.7), (1.7, 1.7); and
fourth extending triangular region: (2.3, 1.5), (1.7, 1.3), (1.7, 1.7).

In some embodiments, provided methods further include steps of providing a third view of the region of tissue; and calculating a third fractal dimension for the third view of the region of tissue; wherein if the fractal dimension of at least one of the first fractal dimension, the second fractal dimension, and the third fractal dimension is in the fractal zone, the region of tissue is considered cancerous. In some embodiments, a fractal dimension is calculated from two-dimensional data. In some embodiments, a fractal dimension is calculated from three dimensional data (e.g., 3D data cubes).

The methods provided by the present invention may be performed on any tissue. In some embodiments, the tissue is selected from breast tissue, brain tissue, lung tissue, kidney tissue, liver tissue, uterine tissue, dermal tissue, and pancreatic tissue.

As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

Definitions

In order for the present invention to be more readily understood, certain terms are first defined below. Additional definitions for the following terms and other terms are set forth throughout the specification.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Cancer: As used herein, the term "cancer" refers to a group of diseases, all involving unregulated cell growth. Exemplary cancers include, without limitation: Acute lymphoblastic leukemia, Acute myeloid leukemia, Adrenocortical carcinoma; AIDS-related cancers; AIDS-related lymphoma; Anal cancer; Appendix cancer; Astrocytoma, childhood cerebellar or cerebral; Basal cell carcinoma; Bile duct cancer, extrahepatic; Bladder cancer; Bone cancer, Osteosarcoma/Malignant fibrous histiocytoma; Brainstem glioma; Brain tumor; Brain tumor, cerebellar astrocytoma; Brain tumor, cerebral astrocytoma/malignant glioma; Brain tumor, ependymoma; Brain tumor, medulloblastoma; Brain tumor, supratentorial primitive neuroectodermal tumors; Brain tumor, visual pathway and hypothalamic glioma; Breast cancer; Bronchial adenomas/carcinoids; Burkitt lymphoma; Carcinoid tumor, childhood; Carcinoid tumor, gastrointestinal; Carcinoma of unknown primary; Central nervous system lymphoma, primary; Cerebellar astrocytoma, childhood; Cerebral astrocytoma/Malignant glioma, childhood; Cervical cancer; Childhood cancers; Chronic lymphocytic leukemia; Chronic myelogenous leukemia; Chronic myeloproliferative disorders; Colon Cancer; Cutaneous T-cell lymphoma; Desmoplastic small round cell tumor; Endometrial cancer; Ependymoma; Esophageal cancer; Ewing's sarcoma in the Ewing family of tumors; Extracranial germ cell tumor, Childhood; Extragonadal Germ cell tumor; Extrahepatic bile duct cancer; Eye Cancer, Intraocular melanoma; Eye Cancer, Retinoblastoma; Gallbladder cancer; Gastric (Stomach) cancer; Gastrointestinal Carcinoid Tumor; Gastrointestinal stromal tumor (GIST); Germ cell tumor: extracranial, extragonadal, or ovarian; Gestational trophoblastic tumor; Glioma of the brain stem; Glioma, Childhood Cerebral Astrocytoma; Glioma, Childhood Visual Pathway and Hypothalamic; Gastric carcinoid; Hairy cell leukemia; Head and neck cancer; Heart cancer; Hepatocellular (liver) cancer; Hodgkin lymphoma; Hypopharyngeal cancer; Hypothalamic and visual pathway glioma, childhood; Intraocular Melanoma; Islet Cell Carcinoma (Endocrine Pancreas); Kaposi sarcoma; Kidney cancer (renal cell cancer); Laryngeal Cancer; Leukemias; Leukemia, acute lymphoblastic (also called acute lymphocytic leukemia); Leukemia, acute myeloid (also called acute myelogenous leukemia); Leukemia, chronic lymphocytic (also called chronic lymphocytic leukemia); Leukemia, chronic myelogenous (also called chronic myeloid leukemia); Leukemia, hairy cell; Lip and Oral Cavity Cancer;

Liposarcoma; Liver Cancer (Primary); Lung Cancer, Non-Small Cell; Lung Cancer Small Cell Lymphomas; Lymphoma, Burkitt; Lymphoma, cutaneous T-Cell; Lymphoma, Hodgkin; Lymphoma, Primary Central Nervous System; Macroglobulinemia, Waldenström; Malignant Fibrous Histiocytoma of Bone/Osteosarcoma; Medulloblastoma, Childhood; Melanoma; Melanoma, Intraocular (Eye); Merkel Cell Carcinoma; Mesothelioma, Adult Malignant; Mesothelioma, Childhood; Metastatic Squamous Neck Cancer with Occult Primary; Mouth Cancer; Multiple Endocrine Neoplasia Syndrome, Childhood; Multiple Myeloma/Plasma Cell Neoplasm; Mycosis Fungoides; Myelodysplastic Syndromes; Myelodysplastic/Myeloproliferative Diseases; Myelogenous Leukemia, Chronic; Mycloid Leukemia, Adult Acute; Mycloid Leukemia, Childhood Acute; Myeloma, Multiple (Cancer of the Bone-Marrow); Myeloproliferative Disorders, Chronic; Nasal cavity and paranasal sinus cancer; Nasopharyngeal carcinoma; Neuroblastoma; Non-Hodgkin lymphoma; Non-small cell lung cancer; Oral Cancer; Oropharyngeal cancer; Osteosarcoma/malignant fibrous histiocytoma of bone; Ovarian cancer; Ovarian epithelial cancer (Surface epithelial-stromal tumor); Ovarian germ cell tumor; Ovarian low malignant potential tumor; Pancreatic cancer; Pancreatic cancer, islet cell; Paranasal sinus and nasal cavity cancer; Parathyroid cancer; Penile cancer; Pharyngeal cancer; Pheochromocytoma; Pineal astrocytoma; Pineal germinoma; Pineoblastoma and supratentorial primitive neuroectodermal tumors, childhood; Pituitary adenoma; Plasma cell neoplasia/Multiple myeloma; Pleuropulmonary blastoma; Primary central nervous system lymphoma; Prostate cancer; Rectal cancer; Renal cell carcinoma (kidney cancer); Renal pelvis and ureter, transitional cell cancer; Retinoblastoma; Rhabdomyosarcoma, childhood; Salivary gland cancer; Sarcoma, Ewing family of tumors; Sarcoma, Kaposi; Sarcoma, soft tissue; Sarcoma, uterine; Sézary syndrome; Skin cancer (nonmelanoma); Skin carcinoma, Merkel cell; Small intestine cancer; Soft tissue sarcoma; Squamous cell carcinoma; Squamous neck cancer with occult primary, metastatic; Stomach cancer; Supratentorial primitive neuroectodermal tumor, childhood; T-Cell lymphoma, cutaneous; Testicular cancer; Throat cancer; Thymoma, childhood; Thymoma and Thymic carcinoma; Thyroid cancer; Thyroid cancer, childhood; Transitional cell cancer of the renal pelvis and ureter; Trophoblastic tumor, gestational; Unknown primary site, carcinoma of, adult; Unknown primary site, cancer of, childhood; Ureter and renal pelvis, transitional cell cancer; Urethral cancer; Uterine cancer, endometrial; Uterine sarcoma; Vaginal cancer; Visual pathway and hypothalamic glioma, childhood; Vulvar cancer; and Wilms tumor (kidney cancer), childhood.

Pre-Cancer: As used herein the term "pre-cancer" or "pre-cancerous" is used to refer to tissue in or from a subject that is not yet cancerous, but has a higher chance of becoming cancerous that normal tissue.

Risk: As will be understood from context, a "risk" of a disease, disorder, and/or condition comprises a likelihood that a particular individual will develop a disease, disorder, and/or condition (e.g., a cancer). In some embodiments, risk is expressed as a percentage. In some embodiments, risk is from 0,1, 2, 3, 4, 5, 6, 7, 8, 9, 10, 20, 30, 40, 50, 60, 70, 80, 90 up to 100%. In some embodiments risk is expressed as a risk relative to a risk associated with a reference sample or group of reference samples. In some embodiments, a reference sample or group of reference samples have a known risk of a disease, disorder, condition and/or event (e.g., a muscular dystrophy). In some embodiments a reference sample or group of reference samples are from individuals comparable to a particular individual. In some embodiments, relative risk is 0,1, 2, 3, 4, 5, 6, 7, 8, 9, 10, or more.

Subject: As used herein, the term "subject" refers to a human or any non-human animal (e.g., mouse, rat, rabbit, dog, cat, cattle, swine, sheep, horse or primate). A human includes pre and post natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

BRIEF DESCRIPTION OF THE DRAWING

FIG. 7A shows a sample simulated fractional Brownian motion image $B_{H-0.5}(x)$; 7B shows the gradient of the image in 7A is obtained as the modulus of the wavelet transformed using equation 2.10 below; 7C shows maxima chains in blue defined as positions where the WT modulus is locally maximal (i.e. the WTMM) and along these chains in 7C further local maxima are found in red (i.e. the WTMMM); this is then repeated as several different scales, three of which are shown in 7D, 7E, and 7F; the WTMMM were then connected vertically through scales to define the WT skeleton shown in 7G, with the gray-scale coding going from black (minimum) to white (maximum).

DETAILED DESCRIPTION OF CERTAIN EMBODIMENTS

Figure 1:
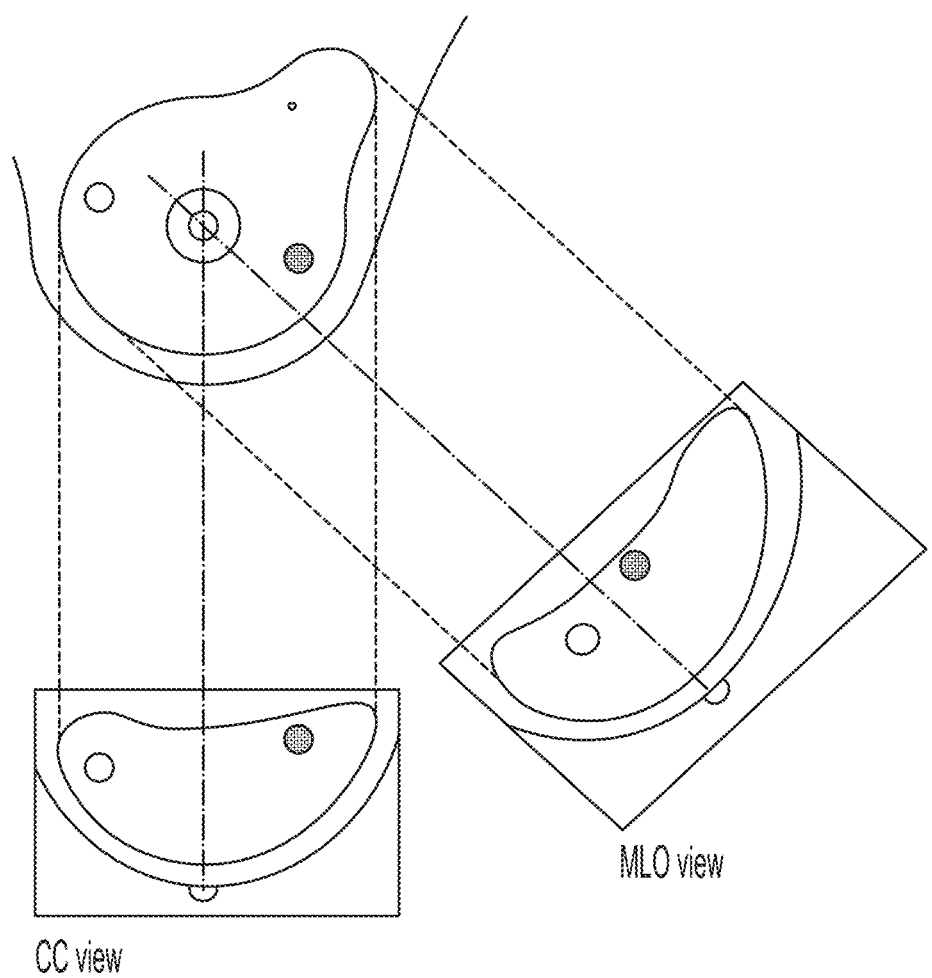
FIG. 1 shows a representative schematic of imaging breast tissue from mediolateral oblique (MLO) and craniocaudal (CC) angles.

The present invention provides, among other things, methods and systems for identifying cancerous or pre-cancerous tissue in a subject. The present invention is based, in part, on the surprising discovery that analysis of tissue surrounding a region of interest rather than tissue from the region of interest itself, may be used to determine if a particular region of tissue is cancerous or pre-cancerous. In some embodiments, the present invention provides, among other things, methods of identifying cancerous or pre-cancerous tissue including providing a first region of tissue from a subject, calculating a roughness exponent for the first region of tissue, and comparing the roughness exponent of the first region of tissue to 0.5, wherein a difference of less than 0.2 (e.g., less than 0.1, less than 0.05) between the roughness exponent of the first region of tissue and 0.5 indicates that the tissue is cancerous or pre-cancerous. In some embodiments, provided methods further comprise treating the tissue adjacent to the first region of tissue if it is cancerous or pre-cancerous.

In some embodiments, the present invention also provides methods including providing a first view of a region of tissue, providing a second view of a region of tissue, calculating a first fractal dimension for the first view of the region of tissue, and calculating a second fractal dimension for the second view of the region of tissue, wherein if the fractal dimension of at least one of the first fractal dimension and the second fractal dimension is in the fractal zone, the region of tissue is considered cancerous.

In some embodiments, it may be advantageous to perform the providing, calculating, and/or comparing steps of provided methods multiple times. In some embodiments, it is contemplated that performing the providing, calculating and comparing steps multiple times will allow for superior characterization of the tissue or the tissue surrounding a tissue region of interest as compared to performing each step a single time according to various embodiments. In some embodiments, the providing, calculating, and comparing steps are each performed a plurality of times. In some embodiments, the plurality of times is at least 10, at least 20, at least 50, at least 100, at least 300, at least 500, or at least 1,000 times. In some embodiments, performing the providing, calculating, and comparing steps multiple times occurs for different regions of the same organ or tissue. In some embodiments, performing the providing, calculating, and comparing steps multiple times occurs for substantially the same region(s) of the same organ or tissue. In some embodiments, performing the providing, calculating, and comparing steps multiple times occurs for different organs or tissues.

Prior Detection Methods

Breast cancer is the most common cancer worldwide according to the World Health Organization (WHO) and the second leading cause of cancer related death among women in the United States. Despite the recent advances in the medical field, the breast cancer rate has continued to increase over the last 30 years. Cancer is easiest to treat when it is found in the early stages of development, making it critical for women to have regular screenings as recommended by the American Cancer Society (ACS). Mammograms are currently one of the most accepted screening processes and have been proven to be successful in detecting microcalcifications (MC), which are small deposits of calcium in breast tissue (about 200 microns in size), and can be an indicator of the early development of breast cancer.

By identifying early breast cancer, the survival rate for the patient increases. Thus, early detection is key for the patient. However, detecting tumors in the early stages of development may not always be easy due to complex tissue composition and the small size of the tumor. Therefore, it's important for radiologists to identify any asymmetric changes in tissue composition in the breast, as it could be a sign of a potential tumor environment. Doctors rely heavily on the use of mammography, especially for screening of older women, making it a very widely accepted form of breast cancer detection.

Although mammograms are currently the most effective way of detecting breast cancer, it remains difficult to interpret mammograms due to high tissue variability and 3D to 2D projection effects. Current practice is to have two expert radiologists read the mammograms to reduce interpretation errors. However, it is not always possible to have access to two radiologist's interpretation due the size of the hospital or the cost. Computer Aided Diagnosis (CAD) systems were developed to assist doctors in analyzing medical images such as mammograms and since the approval of CAD by the Food and Drug Administration (FDA) in 1998 there has been much attention to developing such software. However, many of the current CAD methods rely on tissue homogeneity characterized by the Hurst exponent, meaning the tissue is assumed to be monofractal and uncorrelated. Healthy fatty and dense tissue, shown by dark and light intensities respectively on mammograms, demonstrate how tissue may not be statistically homogeneous and there are many fluctuations of intensity throughout the image. By neglecting to accurately characterize the environment of possible breast lesions, important information is lost. Therefore, many CAD methods are not offering the expected performance, which leads to increase recall rates and can cause false-positives on up to 70% of normal cases, resulting in an increase of unnecessary stress on women.

A key insight to developing a successful CAD is given by recent research which has shown the importance the microenvironment can have on the growth and development of tumors. The environment of cancerous lesions has shown to be able to create a niche around the stem cells, favoring the survival of cancerous stem cells and protecting cells from any treatment or therapy. Thus, differences between normal and cancer stem cells and their interactions with the neighboring tissue may exist and be able to be detected by a CAD at a much larger scale. Therefore, it is critical for the neighboring tissue to be carefully examined and taken into consideration when using or developing a CAD to evaluate mammograms, something not done prior to the present invention.

One limitation of existing CAD is the inability of the software to rate the significance of the findings, similar to the Breast Imaging-Reporting and Data-System (BI-RADS) assessment score given by the radiologist at the time of the mammogram interpretation. As described herein, the two scores provided by the 2D Wavelet-Transform Modulus Maxima (WTMM) method, i.e. the fractal dimension of the MC and the roughness of the tissue surrounding the breast lesion given by the Hurst exponent, have known physical properties and can provide an insight to the invasiveness and severity of the possible lesion. Indeed, one of the several advantages provided by the present invention is the recognition that by examining not only the tumor, but also the microenvironment, important aspects of benign and malignant processes can be evaluated and possibly lead to detection of early cancer or even pre-cancerous tissue.

Characterization of Dense and Fatty Tissues

An important part of interpreting mammograms relies on the ability of radiologists to identify the composition of tissue determined by dense and fatty components. Genetics play a role in determining breast density and radiologists can detect dense tissue as light intensities on an x-ray and fatty tissue as dark intensities. Density decreases with age as a normal process. To help provide radiologists with a uniform scoring system, the American College of Radiology developed an index which ranks density from 1 to 4, ranging from fatty to dense as shown in Table 1.

TABLE 1

Breast Density Score

| Score | Definition |
|---|---|
| 1 | Fatty Tissue |
| 2 | Scattered Fibroglandular |
| 3 | Heterogeneously Dense |
| 4 | Dense Tissue |

By taking into account the tissue composition of the breast, radiologists can more accurately identify suspicious regions. Since tissue composition should be symmetric between both breasts, differing densities maybe a potential sight for a tumor, causing radiologists to pay close attention to these differing areas.

There have been many statistical studies devoted to mammography analysis by using fractal techniques. One such study was conducted by P. Kestener and colleagues using the 2D WTMM method to analyze normal mammary parenchyma. The goal of the Kestener et al. study was to accurately classify mammographic tissue as dense or fatty. There, the images were obtained from the Digital Database for Screening Mammography (DDSM) at the University of South Florida. The databank contains over 2,500 studies made up of normal, benign and malignant mammograms all categorized by an expert radiologist. Each study has two images of each breast, consisting of a mediolateral oblique (MLO) view and cranio-caudal (CC) view with any suspicious region circled by a radiologist. The suspicious region could contain a mass and/or microcalcifications (MC), but only the cases that were classified as normal, i.e. no suspicious area was identified, were looked at in the Kestener et al. study.

After Kestener analyzed 10 images, 5 fatty breasts and 5 dense breasts, from the DDSM website using the 2D WTMM method, their analysis characterized fatty tissue as $H=0.25\pm0.05$ and dense tissue as $H=0.65\pm0.05$.

Both fatty and dense tissue display monofractal scaling behavior, with fatty tissue, $H=[0.20-0.35]$ being the signature of anti-persistent roughness fluctuations and dense tissue, $H=[0.55-0.75]$, the signature of persistent long-range correlations. Note that no tissue classification index exists in $H=(0.35-0.65)$ and healthy breast tissue is composed of only fatty or dense tissue.

Application of Wavelet-Transform Modulus Maxima to Subject Tissue

Various embodiments of the present invention apply wavelet-transform modulus maxima (WTMM) to one or more images of a tissue in order to characterize one or more attributes of the tissue and/or tissue adjacent to the tissue (i.e., the tissue's microenvironment). The present invention evidences the potential of the two dimensional WTMM method to become a powerful tool in interpreting mammograms. The WTMM method has proven to be successful in several fields of applied science, including geology, astrophysics, cellular biology and orthopedic medicine. The method was originally developed as a multifractal formalism to analyze highly complex 1D signals, 2D images, and 3D images. As described in detail herein, the wavelet transform (WT) acts as a mathematical microscope to characterize spatial image information over a continuous range of size scales. It is the gradient vector of the image smoothed by dilated versions of a Gaussian filter. At each size scale, the wavelet transform modulus maxima (WTMM) are defined by the positions where the modulus of the WT is locally maximal. These WTMM are automatically organized as maxima chains at the considered scale. Along each of these chains, further local maxima are found, the WTMM maxima (WTMMM). This process is repeated for all size scales and the WTMMM from each scale are then linked to form the WT skeleton.

The ability to consider vertical lines in the WT skeleton individually is significant, since it allows one to objectively discriminate between lines pointing to the tissue background from those pointing to the lesion by considering how the WT modulus varies as a function of the scale parameter along each line. One can then calculate the so-called singularity spectrum separately for each subset, which then allows consideration of the roughness exponent H, characterizing the tissue background, and the fractal dimension D of the lesion, characterizing the architecture of the lesion, and their microenvironment.

In some embodiments, provided methods make use of an adaptation of a two dimensional WTMM method, specifically, the continuous wavelet transform method, as a mathematical microscope used to characterize the fractal geometry of clusters of microcalcifications (MC) in human tissue (e.g., breast tissue) and/or to determine the roughness of the background tissue (i.e. tissue adjacent to the tissue of interest) seen in mammograms. The WTMM method yields the so-called singularity spectrum, D(h), i.e. the fractal dimension D, of points having a Holder exponent of h. The MC are seen as Dirac singularities by the WTMM method, therefore having Holder exponent value of h=−1. This allows the MC with h~−1 to be abstracted from the background tissue which has h~0.30 for fatty breast tissue and h~0.65 for dense tissue. Thus, the WTMM method is used to perform a segmentation of tissues, in some embodiments, the breast tumor tissue, based on the strength of the singularities composing the mammogram images, and to simultaneously quantify their fractal dimension.

Comparing the results of provided methods applied on several hundred images from a digital databank of mammograms with known radiologist diagnostics, the fractal dimensions of benign and malignant breast lesions are significantly different, with benign having an integer dimension corresponding to a non-invasive Euclidean object and cancer having a non-integer dimension, representing an invasive structure. In addition, the microenvironments characterized by the roughness of the tissue in which the lesions are embedded (i.e., adjacent to) are different for benign and malignant tumors, and provides an insight into the onset and development of breast cancer.

One score provided by the two dimensional WTMM method is the roughness of the tissue surrounding the breast lesion, given by the Hurst exponent, which has known physical properties and can provide an insight to the invasiveness and severity of the possible lesion. By examining not only the tumor but also the microenvironment, important aspects of benign and malignant processes can be evaluated and possibly lead to early detection of cancer or even pre-cancerous tissue. In various embodiments, other multi-scale methods may also be used as an alternative to WTMM including, but not limited to, wavelets leaders, detrended fluctuation analysis, Fourier transform methodologies, and/or any mathematically related and/or similar multi-scale density fluctuation assessment methods yielding an exponent or spectrum of exponents that is similar and/or can complement the use of the Hurst exponent.

The Hurst exponent (or equivalent roughness exponents obtained by similar multi-scale analytical methods) represents, in part, the physical status of the microenvironment of the tissue (e.g., tissue density as determined from roughness fluctuations) and the level of correlation in that physical status across adjacent tissue. In general, if H<0.5, then the roughness fluctuation are considered anti-correlated, while H>0.5 means that the roughness fluctuations are positively correlated. In either case, the physical system of the analyzed tissue is considered to have some form of spatial memory. An H=0.5 means that the roughness fluctuations are un correlated and are thus considered to have no spatial memory.

The present invention encompasses the recognition that an H=0.5, or an H value within some range surrounding 0.5, in some embodiments between about 0.3-0.65, between about 0.35-0.6, between about 0.4-0.6, between about 0.4-0.55, or between about 0.45-0.55, indicates a region of tissue that is potentially cancerous or pre-cancerous. As described above, around H=0.5 the system has a reduced or loss of correlation between roughness fluctuations, indicating a breakdown in order in the system. It is the recognition that this disorder likely indicates a cancerous or pre-cancerous state that is an important aspect of the methods and systems of the present invention.

The present invention recognizes that the results obtained by using the WTMM method on screening mammograms could not only be used as a possible computer-aided detection (CAD) method, but also as a method to further study the biophysics of tumor onset and progression. As described in the Examples below, after all images were analyzed using provided methods, a statistical analysis was performed on all data, which provided us with information on the critical differences between the organization, behavior, and biological and physical processes of both benign and malignant tumors.

Exemplary Mechanics of Characterizing the Local Regularity of Rough Surfaces with the Wavelet Transform Modulus Maxima Method Most of the fractal methods used to analyze mammograms rely on the estimate of the fractal dimension which is related to the Hurst exponent H which statistically characterizes the global roughness of the mammogram landscape. The two dimensional WTMM method accounts for possible fluctuations of the local regularity of a rough surface as defined by the Holder exponent, h of the function $f$ whose graph defines the rough surface under study. The 2D WTMM method provides a way to estimate the D(h) singularity spectrum which provides us with the Hausdorff dimension of the set of points x where the local roughness of the exponent h(x) is h.

This methodology has the ability to be applied to a variety of rough surfaces, such as mammogram landscapes. We will use the term "rough surface" for an irregular surface. This means the surface can be accurately described by a single-valued, self-affine function satisfying the following:

$\forall |x_0=(x_0, y_0) \in \mathbb{R}^2, \forall x=(x, y) \in \mathbb{R}^2$ in the neighborhood of $x_0$, $\exists H \in \mathbb{R}$ such that, for any $\lambda > 0$:

$$f(x_0+\lambda x, y_0+\lambda^a y)-f(x_0, y_0) \approx \lambda^H [f(x_0+x, y_0+y)-f(x_0, y_0)] \quad (2.1)$$

In various embodiments, the Hurst exponent is used to characterize the global roughness of the function under investigation. If H<1, then the function, f, is nowhere differentiable and the smaller the value for H, the more singular and irregular f. Several methods have been used to estimate the Hurst exponent of self-affine functions, but one has to be careful due to the fact that some functions, such as fractal functions, generally display multi-affine properties in the sense that their roughness fluctuates from point to point. To describe these multifractal functions, one needs to change the definition of the Hurst exponent of $f$ to become a local value, $h(x_0)$. Here, h is called the Holder exponent and it provides the strength of the singularity of $f$ at $x_0$. A rigorous definition of the Holder exponent is given by the largest exponent $h(x_0)$ such that there exists a polynomial of degree $n < h(x_0)$ and a constant $C > 0$, such that for any point x in the neighborhood of $x_0$ one has:

$$|f(x)-P_n(x-x_0)| \leq C|x-x_0|^{h(x_0)} \quad (2.2)$$

If $f$ is n times continuously differentiable at the point $x_0$, then one can use the order n Taylor series of $f$ at $x_0$ for the polynomial Pn(x−x0) and prove $h(x_0) > n$. Thus h(x0) measures how irregular the function f is.

Multi-Scale Edge Detection

The edges of the different structures that appear in an image are often the most important features for pattern recognition. Therefore, many computer tools for edge detection look for points where the gradient of the image intensity has a modulus locally maximum in its direction. With an appropriate choice of analyzing wavelets, one can redefine the Canny's multi-scale edge detection in terms of a 2D wavelet transform.

In several embodiments, use of a multi-scale edge detection methodology is desirable to assist in determining the borders of cancerous or pre-cancerous tissue. Below is a brief discussion of exemplary multi-edge detection techniques that may be used in accordance with the present invention.

First, define two wavelets that are the partial derivatives with respect to x and y, respectively:

$$\psi_1(x, y) = \frac{\partial \theta(x, y)}{\partial x}, \psi_2(x, y) = \frac{\partial \theta(x, y)}{\partial y}, \quad (2.3)$$

where θ(x, y) is a 2D smoothing function that is well localized (around x=y=0) and isotropic. For any function $f(x, y)$ that exists in $L^2(R)$ the wavelet transform has two components with respect to $\psi_1$ and $\psi_2$ and can be expressed in vectorial form as:

$$T_\psi[f](b, a) = \begin{pmatrix} T_{\psi_1}[f] = a^2 \int d^2x \psi_1(a^1(x-b))f(x) \\ T_{\psi_2}[f] = a^{-2} \int d^2x \psi_2(a^{-1}(x-b))f(x) \end{pmatrix}. \quad (2.4)$$

After performing an integration by parts, one can obtain $$T_\phi[f](b, a) = a^{-2} \nabla \{\int d^2x \phi(a^{-1}(x-b))f(x)\} \quad (2.5)$$

$$= \nabla \{T_\phi[f](b, a)\} \quad (2.6)$$

$$= \nabla \{\phi_{b,a} * f\}. \quad (2.7)$$

We will take φ(x) to be the Gaussian function:

$$\phi(x, y) = e^{-\frac{(x^2+y^2)}{2}}, \quad (2.8)$$

If ⏀(x) is simply a smoothing function like the Gaussian, then equation 2.7 amounts to define the 2D wavelet transform as the gradient vector of f(x) smoothed by dilated versions of ⏀($a^{-1}$x) of this filter.

We will be referring to the wavelet-transform in terms of the modulus and argument:

$$T_\psi[f](b, a) = (\mathcal{M}_\psi[f](b, a), \mathcal{A}_\psi[f](b, a)). \quad (2.9)$$

where $$\mathcal{M}_\psi[f](b, a) = [(T_{\psi_1}[f](b, a))^2 + (T_{\psi_2}[f](b, a))^2]^{1/2} \quad (2.10)$$

and $$\mathcal{A}_\psi[f](b, a) = (T_{\psi_1}[f](b, a) + iT_{\psi_2}[f](b, a)). \quad (2.11)$$

As originally proposed by Mallat and collaborators, a very efficient way to perform point-wise regularity analysis is to examine the wavelet transform modulus maxima. At any given scale a, the wavelet transform modulus maxima (WTMM) are defined as the points b where the wavelet transform modulus, M [f](b, a), is locally maximum along the gradient direction given by the wavelet transform argument, A [f](b, a). These WTMM, are inflection points of f *⏀$_a$(x) and lie on connected chains called maxima chains. One only needs to record the position of the local maxima of M along the maxima chains and the values of M [f] and A [f] at the corresponding location. At each scale a, the wavelet analysis reduces to record the WTMM maxima (WTMMM) only. They indicate locally the direction where the signal has the sharpest variation and are disposed along connected curves across scales named maxima lines. The wavelet transform skeleton will be defined as the set of maxima lines that converge to the (x; y)-plane in the limit a→0+.

Discussion of Two Dimensional WTMM Method Mechanics

The 2D WTMM method relies upon the space-scale partitioning given by the WT skeleton. Let us define L(a) as the set of maxima lines that exist at the scale a and which contain maxima at any scale a'≤a. The WTMM method consists in defining the following partition functions directly from the WTMMM that belong to the wavelet transform skeleton:

$$\mathcal{Z}(q, a) = \sum_{\mathcal{L} \in L(a)} (\sup_{(x, a') \in \mathcal{L}, a' \leq a} M_\psi[f](x, a'))^q, \quad (2.12)$$

where q ∈ R. Compared to the classical box-counting techniques, the analyzing wavelet, ψ, plays the role of a generalized "oscillating box", the scale, a, defines its size, while the WT skeleton indicates how to position our boxes to obtain a partition at the considered scale. From the analogy that links the multifractal formalism to thermodynamics, one can define the exponent τ(q) from the power law behavior of the partition function:

$$\mathcal{Z}(q, a) \sim a^{\tau(q)}, a \to 0^+ \quad (2.13)$$

Here, q and τ(q) are the inverse temperature and the free energy respectively. This formalism replaces these variables with the Holder exponent, h, and the singularity spectrum, D(h). This means that the D(h) singularity spectrum of $f$ can be determined from the Legendre transform of the partition function scaling exponent τ(q):

$$D(h) = \min_q(qh - \tau(q)). \quad (2.14)$$

From the properties of the Legendre transform, the homogeneous fractal functions that involve singularities of unique Holder exponent $$h = \frac{\partial \tau}{\partial q}$$

are characterized by τ(q) spectrum which is a linear function of q. A nonlinear τ(q) curve is the signature of nonhomogeneous functions that display multifractal properties in the sense that the Holder exponent h(x) is a fluctuating quantity that depends upon the spatial position x.

The computation of the D(h) singularity spectrum, by the Legendre transform, requires first a smoothing of the τ(q) curve. This smoothing process may loss any interesting physics of phase transitions in the scaling properties of fractal functions. One can avoid directly performing the Legendre transform by considering the quantities h and D(h) as mean quantities defined with respect to their Boltzmann weights computed from the WTMMM:

$$W_\psi[f](q, \mathcal{L}, a) = \frac{|\sup_{(x, a') \in \mathcal{L}, a' \le a} \mathcal{M}_\psi[f](x, a')|^q}{\mathcal{Z}(q, a)}, \quad (2.15)$$

where $\mathcal{Z}(q, a)$ is the partition function. then one computes the expectation values:

$$h(q, a) = \sum_{(x, a')} \ln|\sup_{(x, a') \in \mathcal{L}, a' \le a} \mathcal{M}_\psi[f](x, a')| W_\psi[f](q, \mathcal{L}, a), \quad (2.16)$$

and $$D(q, a) = \sum_{(x, a')} W_\psi[f](q, \mathcal{L}, a) \ln(W_\psi[f](q, \mathcal{L}, a)) \quad (2.17)$$

from which one extracts $$h(q) = \lim_{a \to 0^+} h(q, a)/\ln a \quad (2.18)$$

$$D(q) = \lim_{a \to 0^+} D(q, a)/\ln a \quad (2.19)$$

and therefore the D(h) singularity spectrum.

It is important to note that while several provided methods use a two dimensional analysis, it is contemplated as within the scope of the present invention that three dimensional analyses may also be accomplished. For example, provided methods may be used to analyze a three dimensional image generated via tomosynthesis, fluorescence microscopy, computed tomography, magnetic resonance imaging, or other digital methodology.

Figure 6:
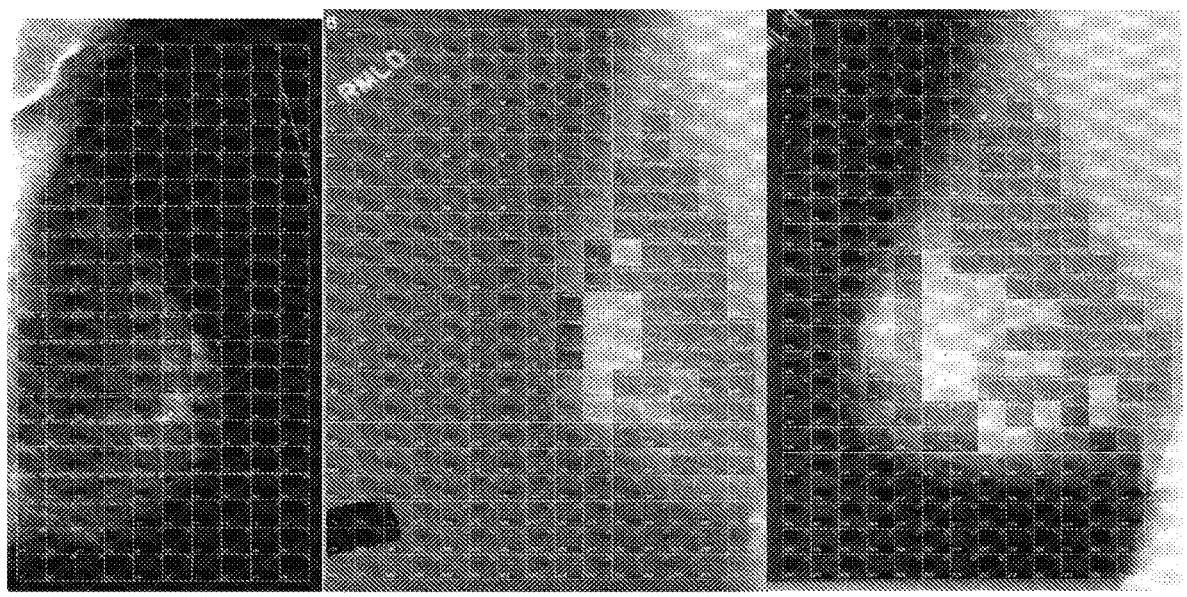
FIG. 6 shows exemplary photographs of breast tissue classified according to provided methods. Specifically, the left panel shows control breast tissue made up of healthy fatty tissue (H<0.45); the center panel shows a breast with a benign lesion lying at the interface between fatty and dense tissue, showing a few surrounding sub-regions of disrupted tissue (yellow, $0.45 \leq H \leq 0.55$); and the right panel shows a breast with a malignant lesion with several disrupted tissue neighboring regions.

In some embodiments, the roughness analysis of tissue is not performed with two dimensional images. The WTMM method as well as all other similar space-scale techniques that allow the calculation of the Hurst exponent (or any analogous exponent), such as, but not limited to wavelet leaders, Fourier techniques, etc are also directly applicable to 3D data cubes. Therefore, the assessment of cancerous or pre-cancerous tissue regions through a roughness analysis is applicable to 3D data. For 3D data the distance between the estimated Hurst exponent (or other analogous exponent) and the critical value 0.5 is the same as for the 2D case. The strategy of analyzing square sub-regions neighboring a tumor or suspicious tissue area such as presented in FIG. 6 is directly generalizable to the analysis of cubic sub-regions in 3D.

Detecting Microcalcifications Through Wavelet Transform Skeleton Segmentation

In addition to determination of roughness exponents, the present invention provides methods and systems for detecting microcalcifications (MC) in subject tissue and characterizing their fractal dimension. In some embodiments, provided methods use two dimensional (or, in some embodiments, three dimensional) WTMM to provide this information, though any mathematically related and/or similar multi-scale density fluctuation assessment method yielding an exponent or spectrum of exponents that is similar and/or can complement the use of the Hurst exponent and/or fractal dimension may be used.

The presence of MC is one of the most important and sometimes the only sign of cancer, for example, breast cancer in a screening mammogram. MCs typically appear as bright spots on mammograms and the number, size, type (Table 2) and distribution (Table 3) provide the radiologist with information about the potential malignancy of the lesion and allow an assessment score (Table 4) to be assigned to each case.

TABLE 2

Calcification Types

| Type | Definition |
|---|---|
| Pleomorphic | Varying in shape and size, smaller than 0.5 mm |
| Punctate | Round 0.5-1 mm |
| Amorphous | Small, round and hazy |
| Fine Linear Branching | Thin and linear or curved. Smaller than 0.5 mm |

TABLE 3

Calcification Distributions

| Distribution | Definition |
|---|---|
| Linear | Arranged in a line, suggesting being deposited in a duct |
| Segmental | Deposits in ducts and branches of a segment or lobe |
| Clustered | At least 5 calcifications in a small volume of tissue |

TABLE 4

BI-RADS Assessment Score

| Score | Interpretation |
|---|---|
| 0 | Cannot be determined by mammogram |
| 1 | No calcifications are present |
| 2 | No evidence of malignancy |
| 3 | Has less than 2% chance of being malignant |
| 4 | Considered suspicious |
| 5 | Has greater than or equal to 95% chance of being malignant |
| 6 | Shown to be malignant through biopsy |

By using the information listed in the above tables, radiologists can predict the potential malignancy of the identified tumor on the mammogram. For example, tumors that contain pleomorphic or fine linear branching calcification types have a higher risk of being malignant than tumors that are classified as punctate. However, it is not uncommon for tumors to be made up of components that make it difficult for radiologists to the identify the tumor as cancerous or a benign disease such as fibrocystic breast condition or a blunt injury. One benefit of a CAD is the objectivity of the software of having a range of indices associated with benign and/or malignant tumors.

Identifying Microcalcifications (MC)

In some embodiments, the present invention provides computer aided diagnostic tools, using the WT methodology to detect MC by inspecting the WT maxima chains. At the smallest scale resolved by the WT microscope, 7 pixels, MC which can be considered at strong singularities are contour-shaped by some maxima chains. Since the average size of MC is about 200 µm, or 5 pixels, these singularities are identified by the mathematical microscope as Dirac singularities. Thus, the corresponding maxima lines pointing to the MC are likely to display scaling properties with a Holder exponent $h=-1$ down to scales of the order of the MC size where one can observe a cross-over to the value $h=0$ as the signature of the MC boundary. Therefore, one can perform a classification of these lines according to the behavior of the $M_\psi$ [f] and then separate MC, $h=-1$, from dense tissue, $h\sim0.65$, and fatty tissue, $h\sim0.30$.

As pointed out above, the MC wavelet-transform skeleton can be used to compute the partition functions, and thus fully characterize the fractal geometry of the MC cluster.

Separating the MC from the subject tissue (e.g., breast tissue) in this way is key, since it allows one to consider the properties of the background tissue separate from the properties of the MC. Using provided methods, one is able to quantify the arrangement and organization of the MC and consider the distribution of the tumor, making the similar information currently used in Table 3 less subjective. At the same time, one can classify the tissue and analyze any interesting physical or structural changes from previous mammograms or surrounding tissue. Therefore, the two dimensional WTMM method has the ability to be a powerful CAD. The information obtained from the wavelet-transform analysis can help quantify data that would otherwise be considered subjective. In some embodiments, provided methods use this information to aid in the development of an objective mammographic classification, which can be used to judge the potential malignancy of a radiologist-identified suspicious region.

Assessment of Three Dimensional Fractal Geometry from Multiple Two Dimensional Views In some embodiments, characterization of the fractal geometry of MC clusters from a plurality of separate two-dimensional views of the same region of tissue (e.g. a breast), allows for an assessment of the overall fractal dimension of the tissue region of interest, such as through application of the WT methods described herein. In other words, according to various embodiments, by using a plurality of separate two-dimensional views of the same region of tissue one can assess the fractal dimension of the three dimensional tissue region of interest. These concepts are described in more detail in the Examples below.

In some embodiments, non-cancerous or non-pre-cancerous tissue will have a Euclidean fractal dimension (i.e. an integer fractal dimension). In some embodiments, a cancerous or pre-cancerous tissue will have a non-integer fractal dimension indicating an invasive morphology.

In some embodiments, the present invention also provides methods including providing a first view of a region of tissue, providing a second view of a region of tissue, calculating a first fractal dimension for the first view of the region of tissue, and calculating a second fractal dimension for the second view of the region of tissue, wherein if the fractal dimension of at least one of the first fractal dimension and the second fractal dimension is in the fractal zone, the region of tissue is considered cancerous. In some embodiments, provided methods further comprise treating the region of tissue if it is cancerous or pre-cancerous.

In some embodiments, the "fractal zone" is defined as a polygon consisting of a central square and a first, second, third, and fourth extending triangular region as plotted on a graph of the fractal dimension of the first view of the region of tissue by the fractal dimension of the second view of the region of tissue.

Figure 11:
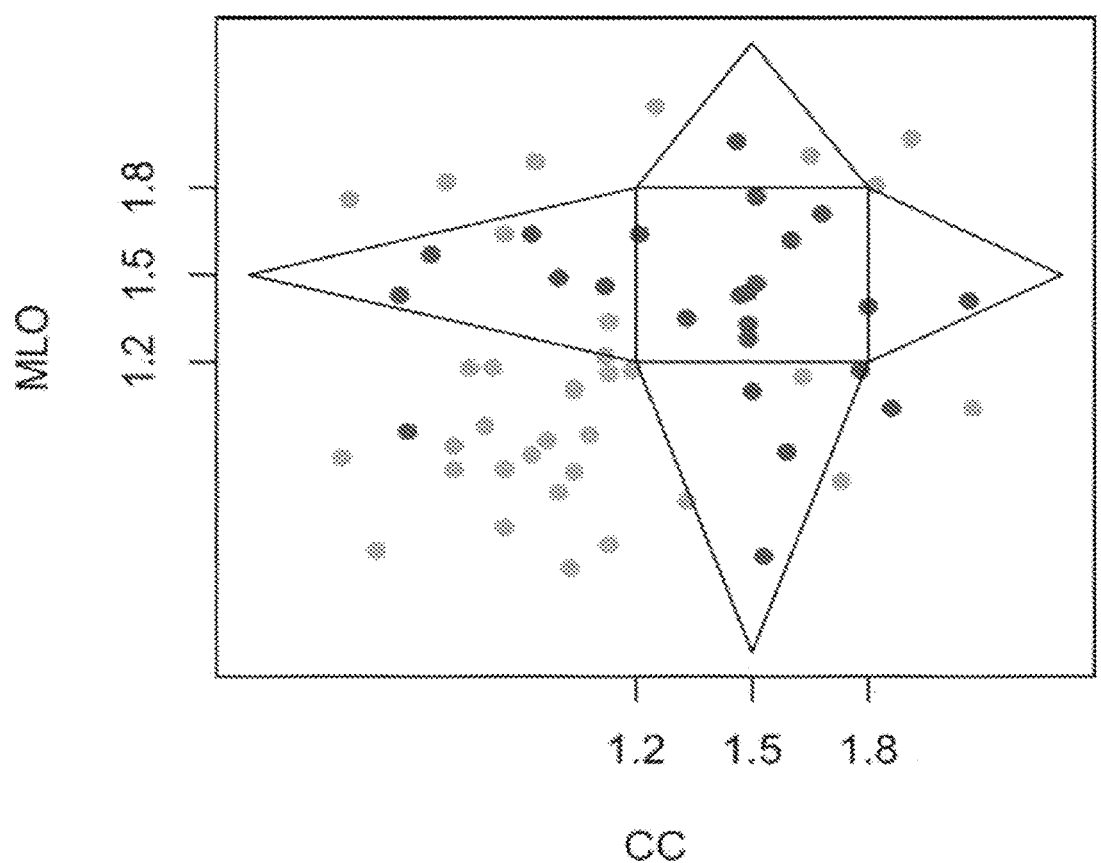
FIG. 11 shows a fractal dimension plot of several samples; specifically, each case is represented by a single dot and is plotted with the fractal dimension obtained from the mediolateral oblique (MLO) view as a function of the fractal dimension obtained from the cranio-caudal (CC) view. A polygonal region is outlined, the inside of which is defined as the "fractal zone" while the outside is defined as the "Euclidean zone". The dots represent malignant (dark red) and benign (light green) cases.

In order to provide greater clarity around the concept of fractal zones, several non-limiting exemplary embodiments are provided. In some embodiments, such as that shown in FIG. 11, a fractal zone may be defined as consisting of a central square and a first, second, third, and fourth extending triangular region as plotted on a graph of the fractal dimension of the first view of the region of tissue by the fractal dimension of the second view of the region of tissue with the following dimensions:

central square: (1.2, 1.2), (1.2, 1.8), (1.8, 1.2)(1.8, 1.8);

first extending triangular region: (0.5, 1.5), (1.2, 1.2), (1.2, 1.8);

second extending triangular region: (1.5, 0.5), (1.2, 1.2), (1.8, 1.2);

third extending triangular region: (1.5, 2.3), (1.2, 1.8), (1.8, 1.8); and fourth extending triangular region: (2.3, 1.5), (1.8, 1.2), (1.8, 1.8).

In some embodiments, a fractal zone may be defined as consisting of a central square and a first, second, third, and fourth extending triangular region as plotted on a graph of the fractal dimension of the first view of the region of tissue by the fractal dimension of the second view of the region of tissue with the following dimensions:

central square: (1.1, 1.1), (1.1, 1.9), (1.9, 1.1)(1.9, 1.9);

first extending triangular region: (0.5, 1.5), (1.1, 1.1), (1.1, 1.9);

second extending triangular region: (1.5, 0.5), (1.1, 1.1), (1.9, 1.1);

third extending triangular region: (1.5, 2.3), (1.1, 1.9), (1.9, 1.9); and fourth extending triangular region: (2.3, 1.5), (1.9, 1.1), (1.9, 1.9).

In some embodiments, a fractal zone may be defined as consisting of a central square and a first, second, third, and fourth extending triangular region as plotted on a graph of the fractal dimension of the first view of the region of tissue by the fractal dimension of the second view of the region of tissue with the following dimensions:

central square: (1.3, 1.3), (1.3, 1.7), (1.7, 1.3)(1.7, 1.7);

first extending triangular region: (0.5, 1.5), (1.3, 1.3), (1.3, 1.7);

second extending triangular region: (1.5, 0.5), (1.3, 1.3), (1.7, 1.3);

third extending triangular region: (1.5, 2.3), (1.3, 1.7), (1.7, 1.7); and fourth extending triangular region: (2.3, 1.5), (1.7, 1.3), (1.7, 1.7).

It is contemplated that the precise boundaries of the fractal zone may vary according to tissue type and/or tumor type (or subtype). Additionally, without wishing to be held to a particular theory it is possible that the precise borders of the fractal zone may change over time as tissue changes from normal tissue to pre-cancerous or cancerous tissue. One of skill in the art will be able to ascertain from the present disclosure how to determine the appropriate boundaries of the fractal zone in a particular clinical scenario using no more than routine experimentation.

In some embodiments, provided methods may be applied to more than two views of a tissue region of interest. In some embodiments, provided methods may be applied to three, four, five, six, seven, eight, nine, ten, fifteen, twenty or more views of a particular tissue region of interest. One of skill will understand how the addition of additional two-dimension images to the analysis of provided methods will alter the definition of the fractal zone. For example, if three views of a tissue region of interest are used, the fractal zone may then be defined as the union of seven juxtaposed regions: one central cube and six extending pyramidal or conical regions. In some embodiments, wherein four or more views of a tissue region of interest are used, it may be more convenient to define the fractal zone purely mathematically, rather than in terms of geometric shapes. Additionally, the borders of the fractal zone, though described herein (including in the below Examples) as lines, may comprise other forms and definitions. For example, in some embodiments, the borders of the fractal zone may be smooth curves, jagged lines, or even fractals.

In addition to the use of the WTMM method to calculate the fractal dimension of clusters of microcalcifications, other methods may also be used according to various embodiments. In some embodiments, any fractal technique or techniques yielding a fractal dimension, such as, but not limited to: box-counting techniques, the perimeter-area relationship, packing dimension, Hausdorff dimension, capacity dimension, correlation dimension, the generalized dimensions (multifractal), and/or any space-scale technique that yields a value quantifying the structural complexity of a tumor or object of interest as a function of scale may be used.

As described elsewhere herein, provided methods may be applied to any tissue that may contain or comprise cancer. Non-limiting exemplary such tissues include breast tissue, brain tissue, lung tissue, kidney tissue, liver tissue, uterine tissue, dermal tissue, and pancreatic tissue.

Treatment of Cancerous or Pre-Cancerous Tissue

According to various embodiments, provided methods may be used to detect and/or characterize the presence of cancerous or pre-cancerous tissue in a subject. It is contemplated that if cancerous or pre-cancerous tissue is discovered, that treatment of such tissue would commence in accordance with sound medical judgment. It is further contemplated that treatment may occur with any anti-cancer therapy, whether currently known or discovered in the future.

While any anti-cancer therapy may be appropriate for use in some embodiments, exemplary types of anti-cancer therapy are described below in order to better illustrate some of the principles of the present invention.

Traditional therapies or anticancer agents include surgery, radiotherapy (γ-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Mcthotrcxatc), purinc antagonists and pyrimidinc antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), to name a few. Any and all of these exemplary therapies, as well as other cancer therapies known by one of skill in the art, may be used in connection with the present invention.

It is contemplated that the specific treatment, including dose, dosing regimen, mode of administration, and timing of the onset and termination of therapy will be determined by a medical practitioner in accordance with sound medical judgment.

Systems and Devices for Implementing Provided Methods

The present invention also provides systems and devices, such as computing devices, implementing provided methods. In some embodiments, a computing device maybe a cloud computing device, a mobile computing device, or any other application-appropriate computing device.

Figure 13:
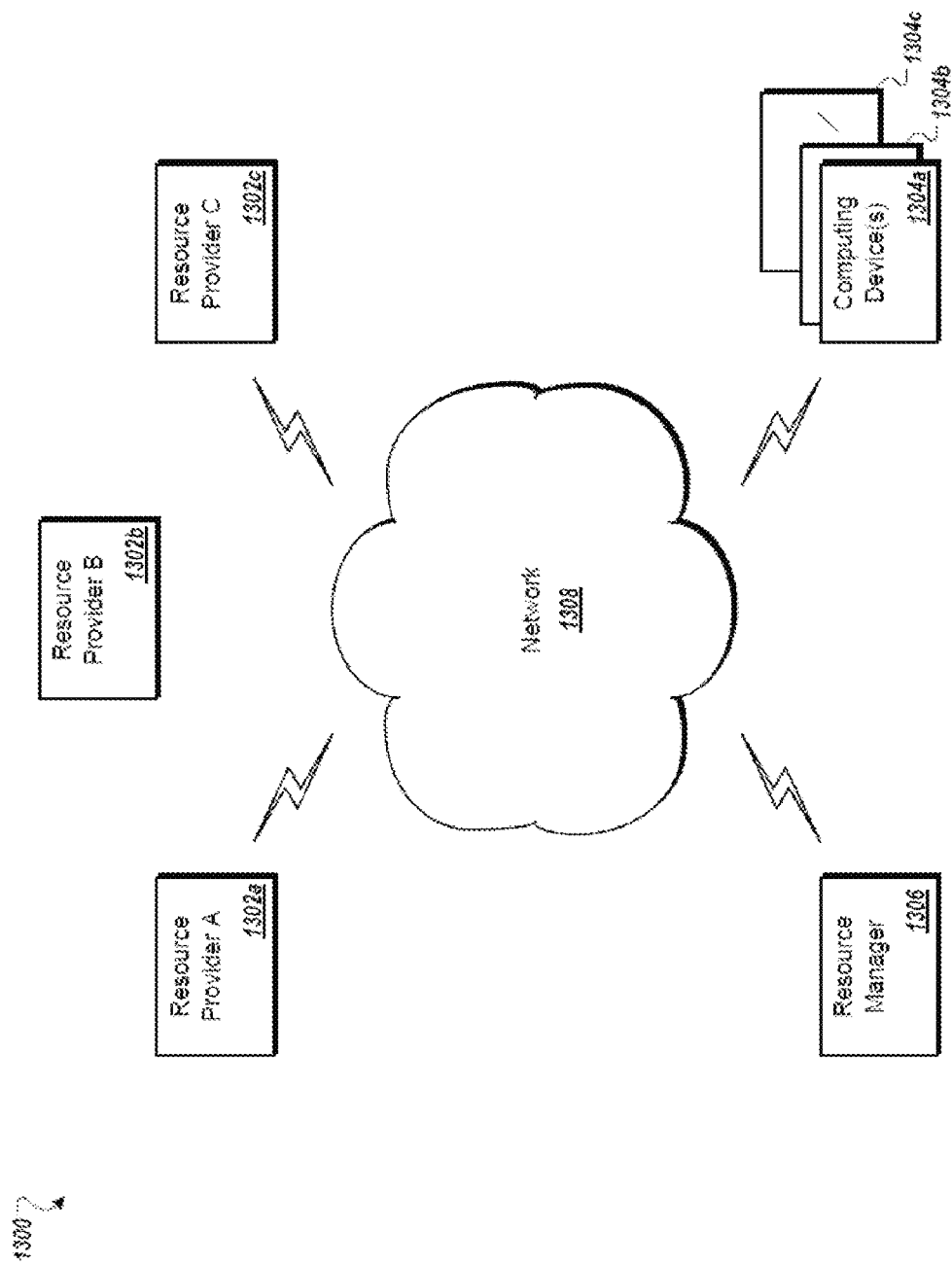
FIG. 13 shows a block diagram of an exemplary cloud computing environment suitable for use with provided methods.

As shown in FIG. 13, an exemplary implementation of a network environment 1300 for use with provided methods is shown and described. In brief overview, referring now to FIG. 13, a block diagram of an exemplary cloud computing environment 1300 is shown and described. The cloud computing environment 1300 may include one or more resource providers 1302a, 1302b, 1302c (collectively, 1302). Each resource provider 1302 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 1302 may be connected to any other resource provider 1302 in the cloud computing environment 1300. In some implementations, the resource providers 1302 may be connected over a computer network 1308. Each resource provider 1302 may be connected to one or more computing device 1304a, 1304b, 1304c (collectively, 1304), over the computer network 1308.

The cloud computing environment 1300 may include a resource manager 1306. The resource manager 1306 may be connected to the resource providers 1302 and the computing devices 1304 over the computer network 1308. In some implementations, the resource manager 1306 may facilitate the provision of computing resources by one or more resource providers 1302 to one or more computing devices 1304. The resource manager 1306 may receive a request for a computing resource from a particular computing device 1304. The resource manager 1306 may identify one or more resource providers 1302 capable of providing the computing resource requested by the computing device 1304. The resource manager 1306 may select a resource provider 1302 to provide the computing resource. The resource manager 1306 may facilitate a connection between the resource provider 1302 and a particular computing device 1304. In some implementations, the resource manager 1306 may establish a connection between a particular resource provider 1302 and a particular computing device 1304. In some implementations, the resource manager 1306 may redirect a particular computing device 1304 to a particular resource provider 1302 with the requested computing resource.

Figure 14:
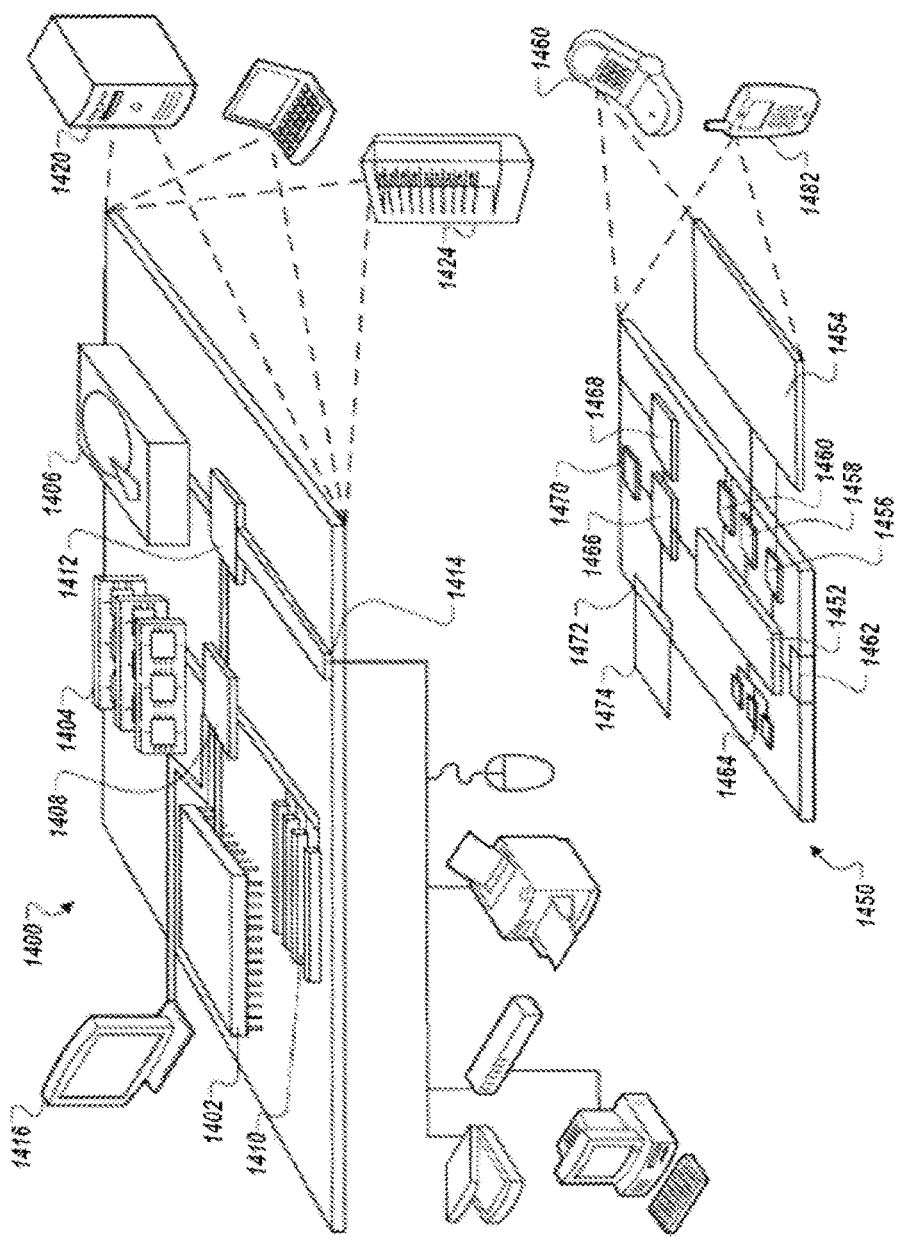
FIG. 14 is a block diagram of an exemplary computing device and a mobile computing device suitable for use with provided methods.

FIG. 14 shows an example of a computing device 1400 and a mobile computing device 1450 that can be used to implement the techniques described in this disclosure. The computing device 1400 is intended to represent various forms of digital computers, such as laptops, desktops, workstations, personal digital assistants, servers, blade servers, mainframes, and other appropriate computers. The mobile computing device 1450 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 1400 includes a processor 1402, a memory 1404, a storage device 1406, a high-speed interface 1408 connecting to the memory 1404 and multiple high-speed expansion ports 1410, and a low-speed interface 1412 connecting to a low-speed expansion port 1414 and the storage device 1406. Each of the processor 1402, the memory 1404, the storage device 1406, the high-speed interface 1408, the high-speed expansion ports 1410, and the low-speed interface 1412, are interconnected using various busses, and may be mounted on a common motherboard or in other manners as appropriate. The processor 1402 can process instructions for execution within the computing device 1400, including instructions stored in the memory 1404 or on the storage device 1406 to display graphical information for a GUI on an external input/output device, such as a display 1416 coupled to the high-speed interface 1408. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 1404 stores information within the computing device 1400. In some implementations, the memory 1404 is a volatile memory unit or units. In some implementations, the memory 1404 is a non-volatile memory unit or units. The memory 1404 may also be another form of computer-readable medium, such as a magnetic or optical disk.

The storage device 1406 is capable of providing mass storage for the computing device 1400. In some implementations, the storage device 1406 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 1402), perform one or more methods, such as those described above. The instructions can also be stored by one or more storage devices such as computer- or machine-readable mediums (for example, the memory 1404, the storage device 1406, or memory on the processor 1402).

The high-speed interface 1408 manages bandwidth-intensive operations for the computing device 1400, while the low-speed interface 1412 manages lower bandwidth-intensive operations. Such allocation of functions is an example only. In some implementations, the high-speed interface 1408 is coupled to the memory 1404, the display 1416 (e.g., through a graphics processor or accelerator), and to the high-speed expansion ports 1410, which may accept various expansion cards (not shown). In the implementation, the low-speed interface 1412 is coupled to the storage device 1406 and the low-speed expansion port 1414. The low-speed expansion port 1414, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 1400 may be implemented in a number of different forms, as shown in the figure. For example, it may be implemented as a standard server 1420, or multiple times in a group of such servers. In addition, it may be implemented in a personal computer such as a laptop computer 1422. It may also be implemented as part of a rack server system 1424. Alternatively, components from the computing device 1400 may be combined with other components in a mobile device (not shown), such as a mobile computing device 1450. Each of such devices may contain one or more of the computing device 1400 and the mobile computing device 1450, and an entire system may be made up of multiple computing devices communicating with each other.

The mobile computing device 1450 includes a processor 1452, a memory 1464, an input/output device such as a display 1454, a communication interface 1466, and a transceiver 1468, among other components. The mobile computing device 1450 may also be provided with a storage device, such as a micro-drive or other device, to provide additional storage. Each of the processor 1452, the memory 1464, the display 1454, the communication interface 1466, and the transceiver 1468, are interconnected using various buses, and several of the components may be mounted on a common motherboard or in other manners as appropriate.

The processor 1452 can execute instructions within the mobile computing device 1450, including instructions stored in the memory 1464. The processor 1452 may be implemented as a chipset of chips that include separate and multiple analog and digital processors. The processor 1452 may provide, for example, for coordination of the other components of the mobile computing device 1450, such as control of user interfaces, applications run by the mobile computing device 1450, and wireless communication by the mobile computing device 1450.

The processor 1452 may communicate with a user through a control interface 1458 and a display interface 1456 coupled to the display 1454. The display 1454 may be, for example, a TFT (Thin-Film-Transistor Liquid Crystal Display) display or an OLED (Organic Light Emitting Diode) display, or other appropriate display technology. The display interface 1456 may comprise appropriate circuitry for driving the display 1454 to present graphical and other information to a user. The control interface 1458 may receive commands from a user and convert them for submission to the processor 1452. In addition, an external interface 1462 may provide communication with the processor 1452, so as to enable near area communication of the mobile computing device 1450 with other devices. The external interface 1462 may provide, for example, for wired communication in some implementations, or for wireless communication in other implementations, and multiple interfaces may also be used.

The memory 1464 stores information within the mobile computing device 1450. The memory 1464 can be implemented as one or more of a computer-readable medium or media, a volatile memory unit or units, or a non-volatile memory unit or units. An expansion memory 1474 may also be provided and connected to the mobile computing device 1450 through an expansion interface 1472, which may include, for example, a SIMM (Single In Line Memory Module) card interface. The expansion memory 1474 may provide extra storage space for the mobile computing device 1450, or may also store applications or other information for the mobile computing device 1450. Specifically, the expansion memory 1474 may include instructions to carry out or supplement the processes described above, and may include secure information also. Thus, for example, the expansion memory 1474 may be provided as a security module for the mobile computing device 1450, and may be programmed with instructions that permit secure use of the mobile computing device 1450. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier and, when executed by one or more processing devices (for example, processor 1452), perform one or more methods, such as those described above. The instructions can also be stored by one or more storage devices, such as one or more computer- or machine-readable mediums (for example, the memory 1464, the expansion memory 1474, or memory on the processor 1452). In some implementations, the instructions can be received in a propagated signal, for example, over the transceiver 1468 or the external interface 1462.

The mobile computing device 1450 may communicate wirelessly through the communication interface 1466, which may include digital signal processing circuitry where necessary. The communication interface 1466 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 1468 using a radio-frequency. In addition, short-range communication may occur, such as using a Bluetooth®, Wi-Fi™, or other such transceiver (not shown). In addition, a GPS (Global Positioning System) receiver module 1470 may provide additional navigation- and location-related wireless data to the mobile computing device 1450, which may be used as appropriate by applications running on the mobile computing device 1450.

The mobile computing device 1450 may also communicate audibly using an audio codec 1460, which may receive spoken information from a user and convert it to usable digital information. The audio codec 1460 may likewise generate audible sound for a user, such as through a speaker, e.g., in a handset of the mobile computing device 1450. Such sound may include sound from voice telephone calls, may include recorded sound (e.g., voice messages, music files, etc.) and may also include sound generated by applications operating on the mobile computing device 1450.

The mobile computing device 1450 may be implemented in a number of different forms, as shown in the figure. For example, it may be implemented as a cellular telephone 1480. It may also be implemented as part of a smart-phone 1482, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In view of the structure, functions and apparatus of the systems and methods described here, in some implementations, systems and methods for characterizing potentially cancerous and/or pre-cancerous tissue are provided. Having described certain implementations of methods and apparatus for provided methods, it will now become apparent to one of skill in the art that other implementations incorporating the concepts of the disclosure may be used. Therefore, the disclosure should not be limited to certain implementations, but rather should be limited only by the spirit and scope of the following claims.

Throughout the description, where apparatus and systems are described as having, including, or comprising specific components, or where processes and methods are described as having, including, or comprising specific steps, it is contemplated that, additionally, there are apparatus, and systems of the disclosed technology that consist essentially of, or consist of, the recited components, and that there are processes and methods according to the disclosed technology that consist essentially of, or consist of, the recited processing steps.

It should be understood that the order of steps or order for performing certain action is immaterial so long as the disclosed technology remains operable. Moreover, two or more steps or actions may be conducted simultaneously.

EXAMPLES

Example 1

Characterization of Breast Tumor Organization

This Example shows that the 2D WTMM method has the ability to characterize breast tumors and their microenvironment. Data was obtained from the Digital Database for Screening Mammography (DDSM), described above. Cases having a suspicious region, i.e. containing a benign or malignant tumor, were considered. From these cases, only cases having one set of microcalcifications were kept for further investigation and masses were disregarded for this analysis. Using the methods described above, we were able to fully characterize the lesion by the fractal dimension of the breast tumor and the roughness of the microenvironment given by the Hurst exponent.

Figure 2:
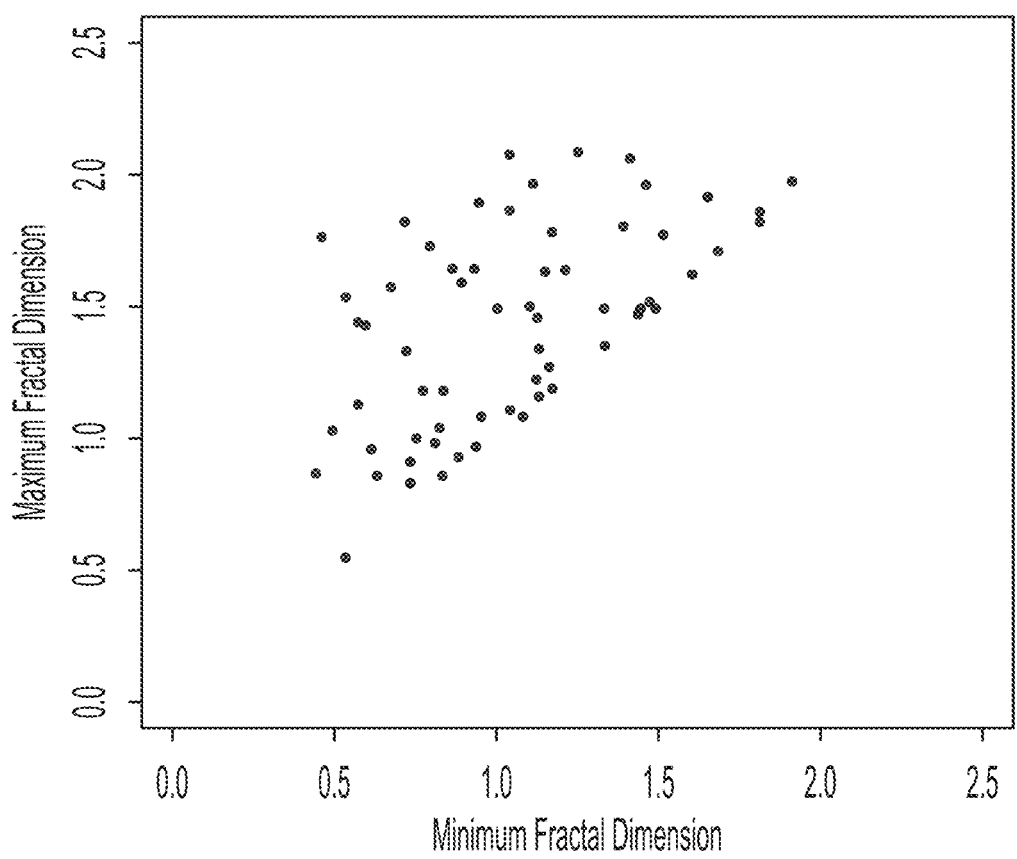
FIG. 2 depicts a graph of the minimum fractal dimension by maximum fractal dimension, with tissue classified according to known methods as benign in blue, and tissue classified according to known methods as malignant tissue, in red.

In this Example, a total of 128 images, 78 of which are benign and 50 of which are malignant, were analyzed. Since each mammographic case contains two images, one corresponding to the mediolateral oblique (MLO) view, and the other to the cranio-caudal (CC) view with their projections shown in FIG. 1, we combined the information to reconstruct an estimate of the 3D structure of the tumor embedded into the breast tissue. The information was combined by creating a scatter plot of the minimum fractal dimension versus the maximum fractal dimension as shown in FIG. 2.

Figure 3:
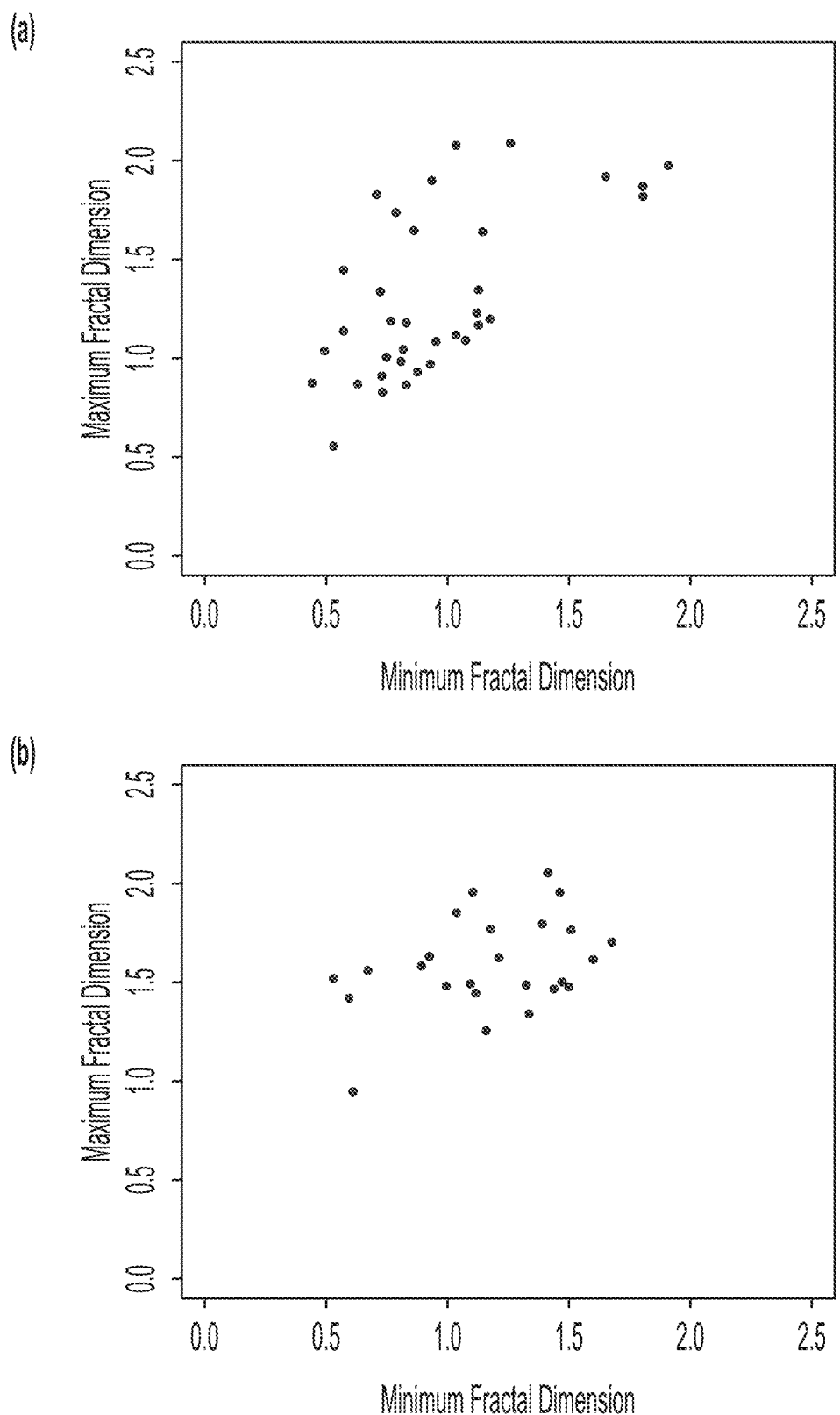
FIG. 3 shows exemplary results of a cluster analysis of scatter plots obtained from graphing minimum fractal dimension by maximum fractal dimension of (a) benign tissue, and (b) malignant tissue.

The Mclust function in R was applied to the two data sets, the benign and malignant scatter plots. The results from the function shown in FIG. 3, suggests that benign tumors are constructed from three subpopulations and malignant tumors are constructed from two subpopulations. Here, it is important to note the centers of the components identified by the function. Benign breast lesions' three components are centered at (0.84,1.04), (0.85,1.78) and (1.78,1.88), while malignant breast lesions' two components are centered at (1.07,1.62) and (1.49,1.52).

The center of the benign categories demonstrate how these tumors are non-invasive since the populations fractal dimensions lay in Euclidean space and are represented by lines, sheets and spheres. However, both malignant categories are shown by invasive fractal dimensions and represented by fractal structures in breast tissue.

Example 2

Classification of Tumor Prone Tissue

This example illustrates how provided methods may be used to better understand the mechanisms that drive the differing organization of benign and malignant tumors, and specifically the microenvironment of a radiologist-identified suspicious region.

To gain a deeper understanding of the behavior and development of breast lesions, neighboring tissue was classified according to the two dimensional WTMM methods described above to survey the microenvironment of the tumors (also see Kestener et al., Wavelet-based multifractal formalism to assist in diagnosis in digitized mammograms, 2001, *Image Anal Stereol*, 20: 169-174 for an application of this methodology). Briefly, the 2D WTMM method was used to analyze mammary parenchyma. This analysis was used to generate a Hurst exponent (H) as a measure of the roughness of a sample. The Hurst score was used to classify breast tissue as fatty (H=0.25±0.05), dense (H=0.65±0.05).

To categorize the neighboring tissue, each image of a breast lesion was segmented into 9 subimages, corresponding to the same size and shape of the radiologist encircled tumor. Once the images were properly segmented, only the central part of the neighboring images were analyzed to counter any edge effects that may disrupt the analysis. The rough surface images were analyzed via the above methodology.

Figure 4:
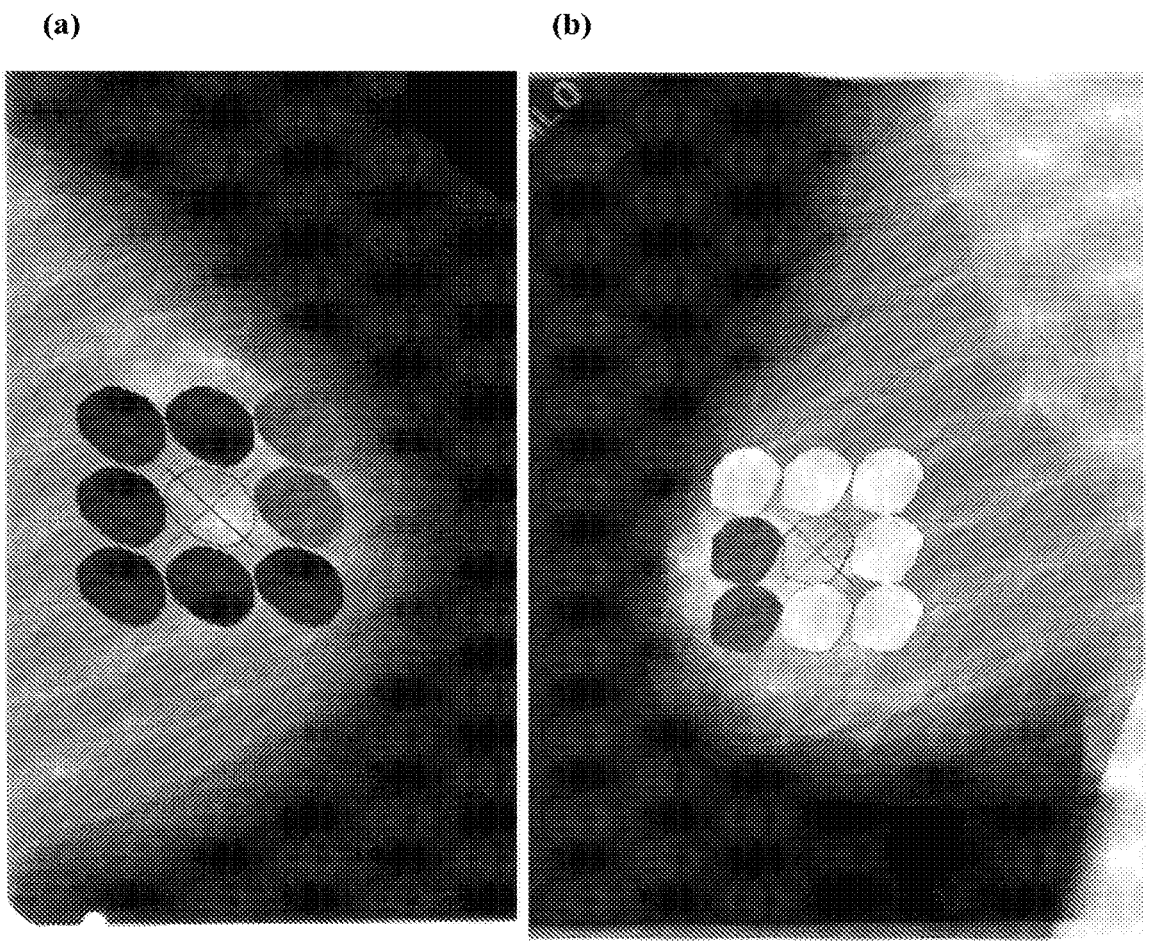
FIG. 4 shows images of breast tissue classified as (a) benign and (b) malignant as classified by provided methods. Note the presence of a majority of disrupted tissue in the image of malignant tissue (represented by yellow circles) and the lack of disrupted tissue in the benign tissue (denoted by a lack of yellow circles).

As shown in FIG. 4, the results allowed for the characterization of abnormal tissue corresponding to a benign tumor and malignant tumor. In FIG. 4, blue represents H=(0-0.45), or fatty tissue, red represents H=(0.55-1), or dense tissue, and yellow represents H=(0.45; 0.55). It is important to note that in the cancer sample shown in FIG. 4 there are several yellow regions identified to have H=(0.45-0.55), where in benign and healthy samples, no such tissue classification was found to exist.

In order to statistically determine if the microenvironments of benign and malignant breast lesions are significantly different, we constructed a t-test to obtain a p-value. Our hypothesis is that the microenvironment of malignant breast tumors are categorized as H=0.5, while benign tumors have a microenvironment categorized as H=0.3 or H=0.65, corresponding to healthy fatty or dense tissue, respectively. We obtained one value per case by averaging the calculating |H −0.5| values of the neighboring tissue for both the CC and MLO views. From here, the H values were averaged for each case. By computing $\Delta H = \langle |H - 0.5| \rangle$, we can expect benign tissue to have a higher value characterizing the microenvironment compared to malignant tissue.

Figure 5:
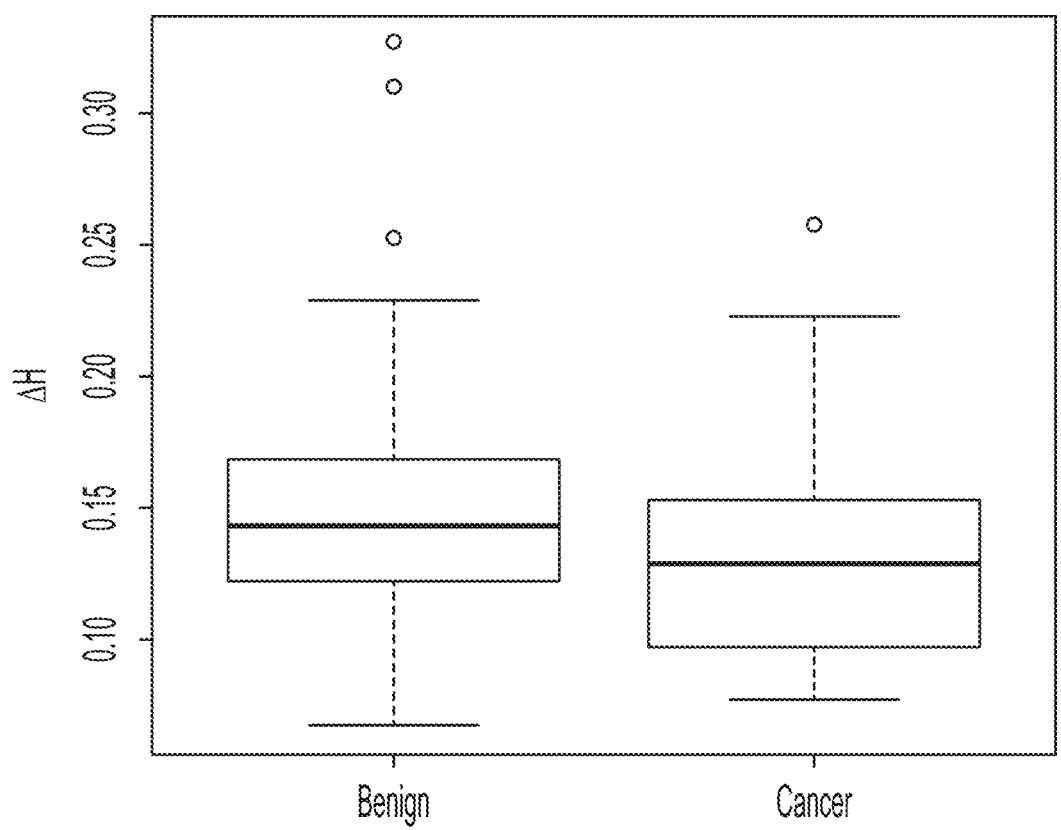
FIG. 5 shows a boxplot of the distribution of AH for both benign and malignant (cancer) tissues.

The boxplot in FIG. 5 shows the distribution of $\Delta H$ for both benign and malignant microenvironments. Here, the max and min values are shown on the plot as 0.33 and 0.07 for benign and 0.26 and 0.08 for cancer respectively. As shown in the boxplot, three outliers were identified for benign and one for cancer, meaning these values for $\Delta H$ are 1.5 times more than the maximum $\Delta H$ value.

Since the boxplot suggests there may be some non-normality of the data, a test for normality was performed in order to decide if a transformation of the data would be necessary before proceeding to the t-test. The Shapiro-Wilk test, first published by S. Shapiro and M. Wilk in 1965, tests the null hypothesis that a sample comes from a normally distributed population. The test statistic is given by:

$$W = \frac{\left(\sum_{i=1}^{n} a_i x_i\right)^2}{\sum_{i=1}^{n} (x_i - \bar{x})^2}, \quad (5.1)$$

where x is the sample mean, $x_{(i)}$ is the i order statistic, and $$a_i = \frac{m^T V^{-1}}{(m^T V^{-1} V^{-1} m)^{\left(\frac{1}{2}\right)}},$$

where $m = (m_1; m_2; \ldots; m_n)_T$ and $m_i$ is expected value of the order statistic and V is the covariance matrix.

The result from performing the Shapiro-Wilk Test on our data shows that the data was not normally distributed since p=0.001 for benign and p=0.033 for cancer. A log transformation was conducted and the results in Table 5 demonstrates normal data.

TABLE 5

Results From Shapiro-Wilk Test

| Group | W | P-Value |
|---|---|---|
| Log (Benign Tissue) | 0.97 | 0.49 |
| Log (Cancer Tissue) | 0.96 | 0.41 |

Once the data has been transfolled in order for the data sets to follow a normal distribution, we checked to make sure the two data sets have equal variances by using the F-ratio test. Here, the null hypothesis is that two normal populations have the same variance. The test statistic is:

$$F = \frac{S_X^2}{S_Y^2}, \quad (5.2)$$

where X and Y are independent and normal, and $S^2_X$ and $S^2_Y$ are the sample variances. Thus, we would reject $H_0$ if F is too large or too small. The results from the F-ratio test in Table 6 tells us to reject $H_0$.

TABLE 6

Results from F-Ratio Test

| F | Numerator df | Denominator df | p-value |
|---|---|---|---|
| 1.04 | 38 | 24 | 0.93 |

Once we have checked the assumptions of the parametric test, we can perform the necessary t-test. We can define $\mu_B$ as ΔH for the benign microenvironment and μC as ΔH for the cancer microenvironment. We will be testing the null hypothesis that $\mu C \geq \mu_B$, making the alternative hypothesis $\mu C < \mu B$. The result, shown in Table 7, was a p-value of 0.04. Thus, we can reject $H_0$ and conclude there is a significant difference in the log(ΔH) values characterizing the microenvironments of benign and malignant breast lesions.

TABLE 7

T-Test Results of Cancer and Benign ΔH

| t | df | p-value |
|---|---|---|
| −1.79 | 52.11 | 0.04 |

It is key to point out that H=0.5 is not found on healthy mammograms in previous studies and less often on the benign sample studied here. Another key piece is that H=0.5 corresponds to no correlation and a loss of structure. This suggests that the tissue composing the environment of malignant tumors has lost its structure and may even precede the onset or progression of the microcalcifications (MC). Thought to be an indicator of the early development of breast cancer. Thus, this Example shows that calculation of a Hurst exponent according to provided methods provides a powerful tool in the early detection and diagnosis of breast cancer.

Example 3

Alternative Analysis of Prone Tissue

As indicated above in Example 2, obtaining one average ΔH value per subject by averaging the calculated |H −0.5| values of neighboring tissue for both the MLO and CC views provided valuable insight that the loss of microenvironmental structure is indicative of the development of tumors, with a higher level of disorder being found in more serious (malignant) tumors.

In this example, rather than calculating a single average ΔH value per subject (consisting of up to 16 neighbors per image, 8 in each of the MLO and CC views), the distribution of ΔH=|H −0.5| for each of the neighboring regions was taken individually. This methodology provides a significantly larger sample size than the analysis in Example 2 because the sample size becomes the number of subjects x the number of neighboring images around each lesion, for a total of (up to) 16 ΔH=|H−0.5| values per subject. When the data in Example 2 is analyzed using this method, the p-value between malignant and benign tissues is an even more significant p=0.001.

The analysis in this Example is likely to be of significant utility in various embodiments because it is better able to account for variations within a subject and may be able to better define cancerous or pre-cancerous regions within a target tissue.

Example 4

Characterization of Tissue Microenvironment

In this Example, data from analyzed breast tissue was characterized on a per neighboring region basis, as opposed to a per patient basis. For this Example, a total of 1,131 images of tissue classified as malignant, 1,131 images of tissue classified as benign, and 64 images of tissue classified as normal were analyzed. Specifically, the number of regions in analyzed microenvironments characterized as fatty, dense or disrupted were calculated from the samples examined in Example 1. Table 8 shows the results of this analysis:

TABLE 8

Classification of Tissue Microenvironment

| Tissue Type | % of images for which H <= 0.45 (FATTY) | % of images for which H > 0.45 and H < 0.55 (DISRUPTED) | % of images for which H >= 0.55 (DENSE) | Total number of images |
|---|---|---|---|---|
| Malignant | 39.8% | 22.6% | 37.6% | 100% |
| Benign | 47.9% | 17.9% | 34.2% | 100% |
| Normal (Healthy) | 51.6% | 10.9% | 37.5% | 100% |

As shown in Table 8, the percentage of disrupted regions was highest in malignant tissue, followed by benign tissue, with normal tissue having the lowest levels of disruption across the tissue. Exemplary photographs of the differences in observed disruption may be found in FIG. 6. It is important to note that the percentage of disrupted regions for normal breast tissue is not 0%. Without wishing to be held to a particular theory, it is possible these disrupted regions may be representative of a transitional state of the tissue that may be prone to the eventual development of a tumor. Longitudinal studies will help to determine the nature of disrupted regions in breast tissue classified as normal by current diagnostic methodologies.

In order to more accurately calculate the proportion of disrupted regions in malignant, benign, and normal tissue (particularly given the low number of normal tissue images analyzed above), a second study of the same design as that described above was performed. In the second study a total of 1,081 malignant images, 1,122 benign images, and 740 images classified as normal (more than ten times that number from the first study) were included. The results are shown below in Table 9:

TABLE 9

Classification of Tissue Microenvironment

| | Normal Tissue | Benign Tissue | Malignant Tissue |
|---|---|---|---|
| Proportion (r) | 44/740 = 5.9% | 202/1,122 = 18.0% | 256/1,081 = 23.7% |
| 95% Confidence Interval | (4.2%-7.6%)* | (15.8%-20.3%)** | (21.1%-26.2%) |

*p = 9.4 × 10$^{-14}$ as compared to benign tissue;
p = 2.2 × 10$^{-16}$ as compared to malignant tissue
**p = 0.0012 as compared to malignant tissue As shown in Table 9, using a larger sample size of tissue classified as normal, the proportion of tissue exhibiting disrupted surrounding regions drops from 10.9% in Table 8 to 5.9% in Table 9. The lower observed proportion of images classified as normal exhibiting disrupted tissue further supports the use of roughness and disorder in surrounding tissue as an indicator of cancer or pre-cancer in a tissue, and possibly malignancy. Without wishing to be held to a particular theory, it is possible that tissue otherwise classified as normal that exhibits some degree of disrupted tissue in the surrounding microenvironment may be pre-cancerous or have an increased likelihood of developing cancer in the future as compared to tissue that does not exhibit disruption in the surrounding microenvironment.

Example 5

Detection of Microcalcification (MC) Clusters and Calculation of their Fractal Dimension Methods—Samples In this Example, images that were analyzed were obtained from the Digital Database for Screening Mammography (DDSM) at the University of South Florida. The databank contains over 2,600 studies made up of normal, benign, benign without call back and malignant mammograms all categorized by an expert radiologist. Each study has two images of each breast, consisting of a mediolateral-oblique (MLO) view and cranio-caudal (CC) view with any suspicious region circled by a radiologist. The suspicious region could contain a mass and/or microcalcifications (MC), but only the cases that were classified as having exactly one tumor composed of only MC in the benign and malignant categories were looked at in this particular study.

In addition to only considering tumors consisting of MC, any mammographic images that contained artifacts inside the radiologist's encircled region were discarded due to the impact it has on the analysis. These artifacts could include scratches, hair, deodorant, patient movement, scanner artifacts (rollers slipped), pacemaker, breast implants, skin markers (for scars, moles, and nipples, as well as marked lumps of breast pain), metallic foreign bodies, and fingerprints. Some (but not all) of these effects were recorded under notes in the DDSM website. In this Example, a total of 59 cases were considered, corresponding to 118 images of size greater than 2562 pixels, 34 of which are benign (68 images) and 25 of which are malignant (50 images).

Methods—The 2D WTMM Method

In this Example, the two dimensional (2D) WTMM method is used to characterize images of breast tissue, as described above. Most of the existing CAD methods, whether specifically designed for two dimensional (2D) mammograms or more recently, for three dimensional (3D) breast tomosynthesis, have been elaborated on the prerequisite that the background roughness fluctuations of normal breast texture are statistically homogeneous and uncorrelated, which precludes their ability to adequately characterize background tissue. The majority of the fractal methods used to examine and classify mammographic breast lesions rely on the estimate of the Hurst exponent (or its various mathematical equivalents), which globally characterizes the self-similar properties of the landscape in question. However, the 2D WTMM method takes in account that the function defining the image may be multifractal, therefore requiring the use of the Holder exponent (M=Ka$^h$) to characterize the local regularity at a particular point.

The 2D WTMM method requires us to define a smoothing function, ∅(x, y), in two dimensions that is a well-localized isotropic function around the origin. In this Example, we used the Gaussian function and define the wavelets as:

$$\psi_1(x, y) = \frac{\partial \phi(x, y)}{\partial x} \text{ and } \psi_2(\bar{x}, \bar{y}) = \frac{\partial \phi(x, y)}{\partial y}.$$

The wavelet transform with respect to $\psi_1$ and $\psi_2$ is $$T_\psi[f](b, a) = \begin{pmatrix} T_{\psi_1}[f] = a^{-2} \int d^2x \psi_1(a^{-1}(x-b))f(x) \\ T_{\psi_2}[f] = a^{-2} \int d^2x \psi_2(a^{-1}(x-b))f(x) \end{pmatrix}$$

$$= T_\psi[f](b, a) = \nabla\{T_\phi[f](b, a)\}$$

from which we can extract the modulus and argument of the WT:

$$T_\psi[f](b, a) = (\mathcal{M}_\psi[f](b, a), \mathcal{A}_\psi[f](b, a))$$

$$\mathcal{M}_\psi[f](b, a) = [(T_{\psi_1}[f](b, a))^2 + (T_{\psi_2}[f](b, a))^2]^{1/2}$$

$$\mathcal{A}_\psi[f](b, a) = Arg(T_{\psi_1}[f](b, a) + i T_{\psi_2}[f](b, a))$$

The wavelet transform modulus maxima are defined as the locations b where $M_\psi[f]$ (b,a) is locally maximum in the direction of the argument $A_\psi$ [f] (b,a), at a given scale a>0. The WTMM lie on connected chains and are thus called maxima chains (FIG. 7A-7F). One can then find the maxima along these WTMM chains. The WTMM maxima, or WTMMM are defined as the points along the maxima chains where the $M_\psi$ [f] (b,a) is locally maximum. The WTMMM are linked through scales to form the space-scale skeleton (FIG. 7G). Hence, one can identify the singularities of the function as the loci x where the WTMMM lines of the WT skeleton (FIG. 7G) point to in the limit a→0⁺. Along these space-scale vertical lines the WTMMM behave as a power-law ~$a^{h(x)}$(M=$ka^h$) from which one can extract the local Hölder exponent h(x). The multifractal formalism amounts to characterize the relative contributions of each Hölder exponent value via the estimate of the so-called D(h) singularity spectrum defined as the fractal dimension of the set of points x where h(x)=h. To compute D(h) we therefore use wavelets to partition the surface by defining the partition function directly from the WTMMM in the skeleton:

$$\mathcal{Z}(q, a) = \Sigma_{\mathcal{L} \in \mathcal{L}(a)} \left( \sup_{(x,a') \in \mathcal{L}, a' \le a} \mathcal{M}_\psi[f](x, a') \right)^q$$

where L(a) is the set of all vertical space-scale lines in the skeleton that exist at the given scale a>0 and which contain maxima at any scale a'≤a and q ε R. One can then define the exponent τ(q) from the power-law behavior of the partition function:

$$\mathcal{Z}(q, a) \sim a^{\tau(q)}, a \to 0^+$$

And the D(h) singularity spectrum of $f$ can be determined from the Legendre transform of the partition function scaling exponent $$D(h) = \min_q(qh - \tau(q))$$

In practice, to avoid instabilities in the estimation of the singularity spectrum D(h) through the Legendre transform, we used h and D(h) as mean quantities defined in a canonical ensemble, i.e. with respect to their Boltzmann weights computed from the WTMMM:

$$W_\psi[f](q, \mathcal{L}, a) = \frac{\left| \sup_{x,a' \in \mathcal{L}, a' \le a} \mathcal{M}_\psi[f](x, a') \right|^q}{\mathcal{Z}(q, a)}$$

Then one computes the expectation values:

$$h(q, a) = \Sigma_{\mathcal{L} \in \mathcal{L}(a)} \ln \left| \sup_{x,a' \in \mathcal{L}, a' \le a} \mathcal{M}_\psi[f](x, a') \right| W_\psi[f](q, \mathcal{L}, a).$$

$$D(q, a) = \Sigma_{\mathcal{L} \in \mathcal{L}(a)} W_\psi[f](q, \mathcal{L}, a) \ln(W_\psi[f](q, \mathcal{L}, a))$$

from which one derives $$h(q) = \frac{d\tau(q)}{dq} = \lim_{a \to 0^+} h(q, a) / \ln a$$

$$D(q) = \lim_{a \to 0^+} D(q, a) / \ln a$$

and thus the singularity spectrum D(h) as a curve parameterized by q.

Homogeneous monofractal functions with singularities of unique Hölder exponent H are characterized by a linear τ(q) curve of slope H. A nonlinear τ(q) is the signature of nonhomogeneous multifractal functions, meaning that the Hölder exponent is a fluctuating quantity that depends on x. Then the corresponding singularity spectrum has a characteristic single-humped shape. Note that for both mono- and multifractal functions $$D(q=0) = -\tau(q=0) = D_F$$

Where $D_F$ (noted simply D throughout the text) is the fractal dimension of the support of singularities of f.

Methods—Statistical Tests

Figure 10:
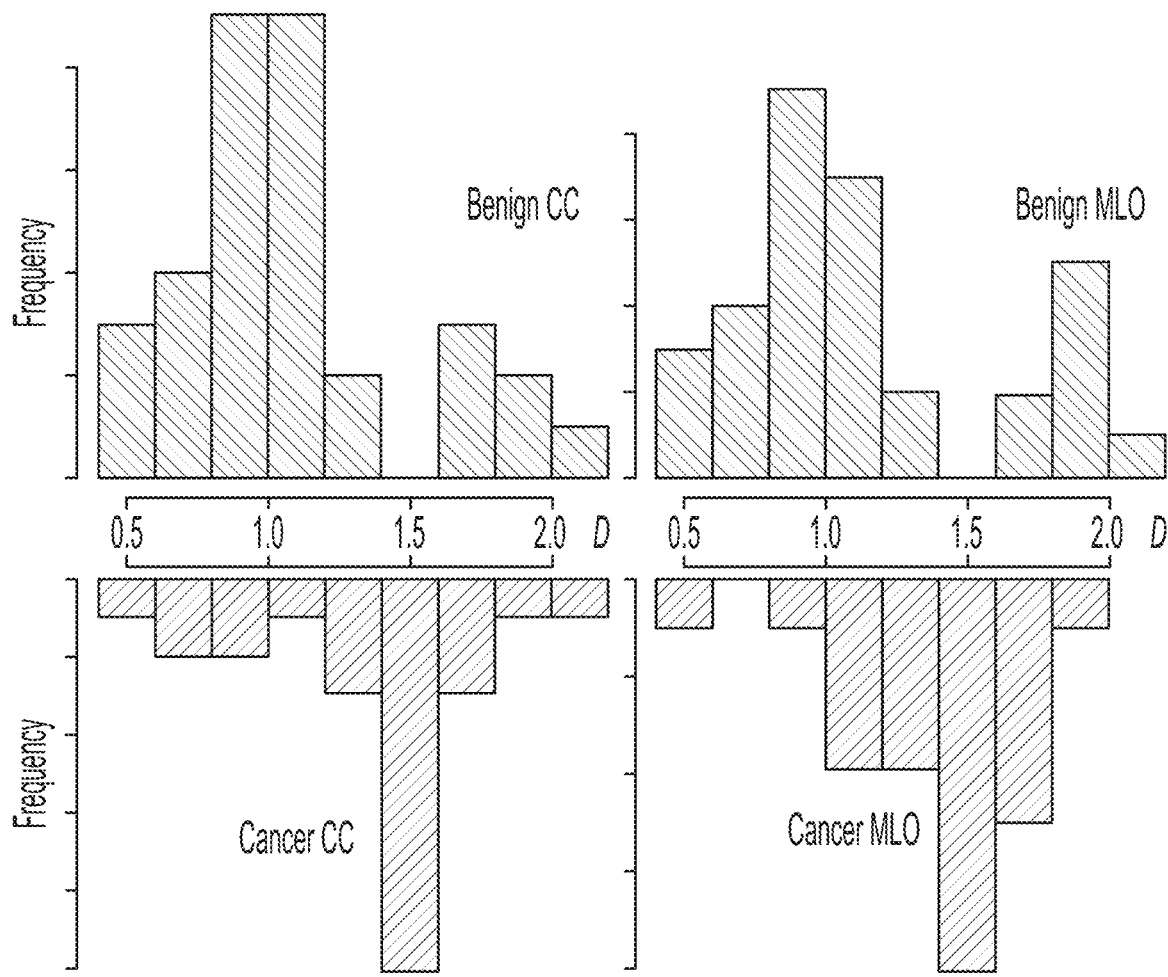
FIG. 10 shows the frequency distributions of fractal dimensions D calculated for benign cranio-caudal (CC) and mediolateral oblique (MLO) views (top panels) as compared to the fractal dimensions D calculated for cancer CC and MLO views (bottom panels); it is of note that the distributions are drastically different between benign and cancer samples.

The Wilcoxon rank-sum test is a non-parametric statistical hypothesis test that is used as an alternative to Student's t-test when the population cannot be assumed to be normally distributed. It was used here to calculate the p-values comparing the CC and MLO fractal dimensions and benign and malignant cases images since the benign data followed a bimodal distribution (FIG. 10). The calculations were done using the Wilcox test in R.

Methods—Bayesian Statistics

Bayes theorem states that $$\underset{\text{posterior}}{p(\theta|G)} = \underset{\text{likelihood}}{p(\theta|G)} * \underset{\text{prior}}{p(\theta)} / \underset{\text{evidence}}{p(G)}$$

where the prior, p(θ), represents the strength of our belief in malignant lesions p(M) or benign lesions p(B) out of those that have been diagnosed by a radiologist. The posterior, p(θ|G), represents the strength of our belief, having accounted for the geometrical evidence, G, where G represents the position of the lesion in the fractal dimension plot, either fractal (F) or Euclidean (E). The quotient of the likelihood over the evidence, p(θ|G)/p(G), represents the support the evidence, G, provides for θ. Since the prior reflects uncertainty in the parameter value θ, p(θ) was based on a Beta distribution with a specified mean and standard deviation. The Beta distribution is as follows:

$$f(\theta; \alpha, \beta) = \frac{\Gamma(\alpha+\beta)}{\Gamma(\alpha)\Gamma(\beta)} \theta^{\alpha-1}(1-\theta)^{\beta-1}$$

The Probability Model: To estimate the mean of the Beta distribution for malignant cases, p(M), the prevalence of mammograms with a BI-RADS assessment score of 3, 4, and 5 were used as determined by the radiologists diagnostics multiplied by the historical probability of mammograms receiving those assessment scores result in malignant MC clusters respectively. One out of the 59 cases considered in this study received an assessment score of 3, 47 out of 59 received a 4, and 11 out of 59 received a 5. Based on historical data, the probability of malignant lesions given an assessment score of 3 is 2%, an assessment score of 4 is 26.5% (taken as the midpoint of the reported interval of

[23%-30%], and an assessment score of 5 is 95%. Therefore the Beta distribution for p(M) was chosen with a mean of $$\frac{1*0.02+47*0.265+11*0.95}{1+47+11}=0.3885$$

and the Beta distribution for p(B) with a mean of 1-0.3885=0.6115. However, since there isn't much certainty regarding these values, the Beta distribution for p(M) and p(B) were assigned a relatively large standard deviation of 0.25. This resulted in a Beta distribution for p(M) with parameters $(\alpha, \beta)$=(1.09241,1.71223) and p(B) with parameters $(\alpha, \beta)$=(1.71223,1.09241). The likelihood p(F|M), where F represents breast lesions characterized as being in the fractal 465 zone (and E likewise represents those in the Euclidean zone), is based on the 23 of the 25 malignant cases that were in the fractal zone; this likelihood is the probability that the data could be generated with parameter values θ. Similarly, the likelihood p(E|B) is based on the 30 out of 34 benign cases that were in the Euclidean zone. To arrive at the posterior distributions p(M|F) and p(B|E), the R routine "BernBeta.R" was used.

The resulting posterior distribution for p(M|F) was a Beta distribution with parameters $(\alpha=24.0924, \beta=3.71223)$. Based on this distribution, the resulting 95% highest density interval was (0.742, 0.975. The posterior distribution for P(B|E) was a Beta distribution with parameters $(\alpha=32.7122, \beta=5.09241)$. Based on this distribution, the resulting 95% highest density interval was (0.757, 0.962). The highest density interval spans 95% of the posterior distribution such that every point inside the interval is deemed more credible. In other words, given the prior and the likelihood, observing the parameter value for the percentage of breast lesions characterized in the fractal zone that are malignant, there is a 95% probability that this parameter is between 0.742 and 0.975. Similarly, for the percentage of breast lesions characterized in the Euclidean zone that are benign, there is a 95% probability that this parameter is between 0.757 and 0.962.

Figure 8A:
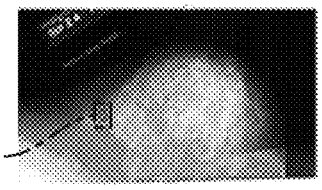
FIG. 8A shows an original image obtained from the DDSM database, and 8B shows a zoomed in image with a suspicious region encircled by a radiologist; by selecting appropriate values for the slope of h of the WT modulus as a function of scale in a logarithmic representation, and the log of the pre-factor, log(k) in 8D, the WTMMM (blue) from the tissue background in 8C are distinguished from the WTMMM (red) that belong to the MC in 8E; from that point the WT skeleton can be calculated from the WTMMM that belong to the lesion from those that belong to the background tissue; the corresponding WTMM chains at the smallest scale are shown in 8F and 8G for the background and lesion, respectively.
Figure 8B:
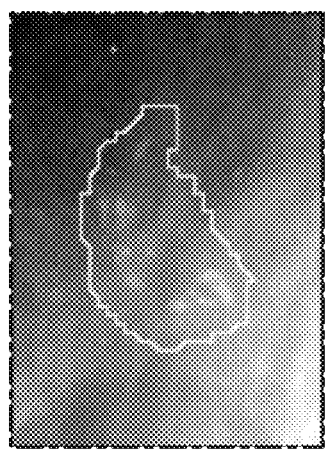
Figure 8C:
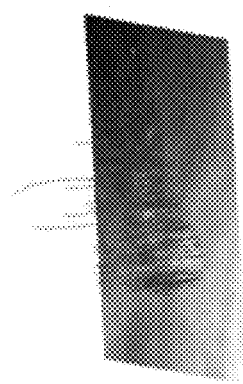
Figure 8D:
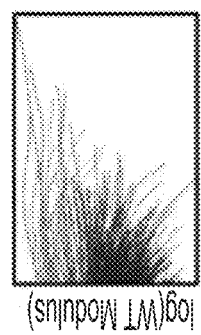
Figure 8E:
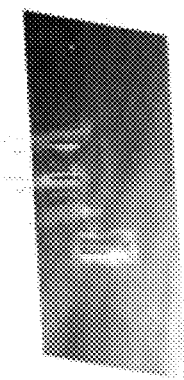
Figure 8F:
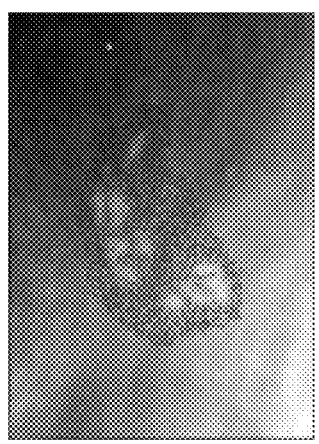
Figure 8G:
Figure 9A:
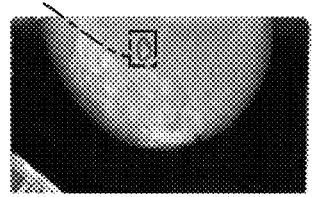
FIG. 9A-G shows the same analysis as in FIG. 8A-G, only on a different case.
Figure 9B:
Figure 9C:
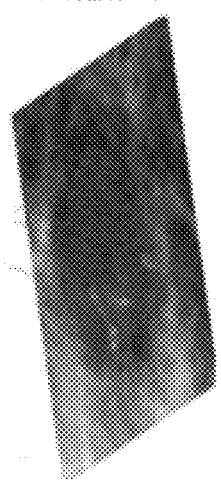
Figure 9D:
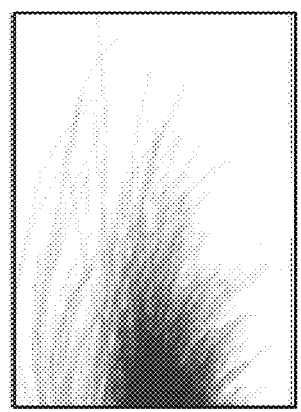
Figure 9E:
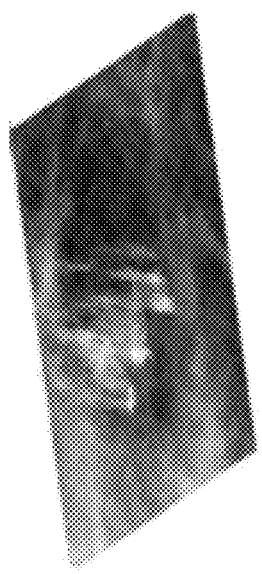
Figure 9F:
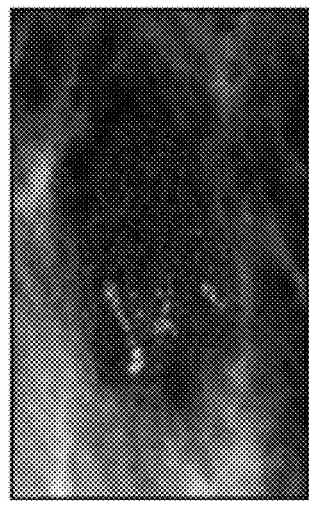
Figure 9G:
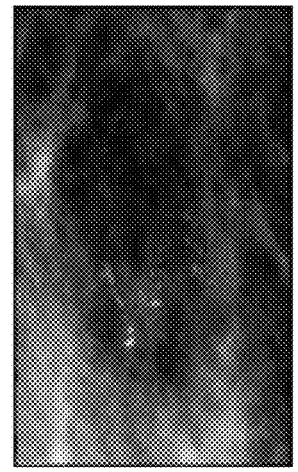

As described in detail in the 2D WTMM Method section and in FIG. 7, the wavelet transform (WT) acts as a mathematical microscope to characterize spatial image information over a continuous range of size scales. It is the gradient vector of the image smoothed by dilated versions of a Gaussian filter. At each size scale, the wavelet transform modulus maxima (WTMM) are defined by the positions where the modulus of the WT is locally maximal. These WTMM are automatically organized as maxima chains at the considered scale. Along each of these chains, further local maxima are found, i.e., the WTMM maxima (WT-MMM). This process is repeated for all size scales and the WTMMM from each scale are then linked to form the WT skeleton. As shown in FIGS. 8 and 9, the ability to consider (vertical) space-scale WTMMM lines in the WT skeleton individually is key, since it allows us to objectively discriminate between lines pointing to the tissue background from those pointing to the microcalcifications by considering how the WT modulus varies as a function of the scale parameter along each space-scale line. In FIGS. 8D and 9D, each space-scale line obtained from the WT skeleton is represented by plotting the evolution of the WT modulus, M (see the 2D WTMM section above), as a function of the scale parameter, a, in a log-log plot. This relationship between M and a is characterized by a power-law behavior via the equation $$M=Ka^h$$

where K is a pre-factor and h is the Holder exponent quantifying the strength of the singularity to which the space-scale line is pointing to. In log-log plots shown in FIGS. 8D and 9D, the slope of the curves therefore corresponds to h. By considering two types of information characterizing the behavior of a space-scale line, namely the strength of the modulus at the smallest scale, which is given by the log of the pre-factor, log(K), as well as the slope (in a logarithmic representation) of the modulus variation across scales, h, a classification procedure is setup which results in two sets of space-scale lines that clearly segregate MC from background tissue. Isolated MC can be seen as Dirac-like singularities through the optics of the WT, for which h is theoretically known to be −1. However, while clustered MC may not appear as isolated 200 Dirac-like singularities, the edge that they form is still easily detectable through the space-scale lines, with a value of h~0 (discontinuity). This means that for both isolated and clustered MC, we can expect the space-scale lines to behave as $M=ka^h$ with h≤0, which contrasts from the healthy background tissue, for which h~1/3 for fatty breast tissue and h~2/3 for dense breast tissue. However, relying only on h may not be sufficient, which is why the strength of the WT modulus at the lowest scale, which quantifies the contrast between MC and background, is also needed. For the sample case presented in FIG. 8, the plot in FIG. 8D shows that neither log(K) nor h, taken individually, would have been sufficient to segregate between MC and background. However, for the sample case presented in FIG. 9, the plot in FIG. 9D shows that log(K) alone was sufficient. A more detailed discussion of both cases follows.

In FIG. 8 the background breast tissue is dense, which makes the contrast between background and MC weak (i.e. causing a low value for the WT modulus of red curves at the smallest scale in FIG. 8D). However, the roughness fluctuations of dense breast tissue are characterized by a relatively high smoothness level, which translates to blue curves with a large slope (i.e., a high h value, ~2/3) for scales 10<a<200 pixels as compared to the red curves with negative slopes for scales a≥10 pixels that correspond to WTMMM lines that point to MC at small scale (a→0+) (FIG. 8D). In FIG. 9, the background breast tissue is fatty, which is characterized by a higher roughness level (i.e. a lower h value ~1/3, although still positive), that reduces the discriminatory power of h. However, for MC embedded into fatty tissue, the contrast is high, which translates to a high value of log(K). Therefore, applying a threshold on both parameters, h and log(K), is key to segregating MC from their background regardless of the density (fatty or dense) of the composition of the breast tissue.

Once this segregation is done, the so-called singularity spectrum can then be calculated separately for each subset, which then allows us to consider the fractal dimension D of the lesion, characterizing its architecture.

We restricted the analysis of DDSM cases (see Methods sections above) to images having a radiologist encircled region that was larger than 2562 pixels for both views (CC and MLO) and also to make sure that the distribution of patient ages was comparable (i.e. 56.7+/−11.4 years old for the benign cases and 65.5+/−12.4 years old for the malignant cases). This resulted in an analyzed sample with a total of 59 cases (118 images), 34 of which are benign (68 images) and 25 of which are malignant (50 images). The histograms of fractal dimension values obtained are presented in FIG. 10. Note that blending the CC and MLO fractal dimensions together in these distributions would not guarantee an unbiased statistical analysis, which is why the fractal dimension values for the CC and MLO results were analyzed independently. FIG. 10 demonstrates that benign MC clusters have a strong preference for Euclidean dimensions that are either close to D=1 or to D=2 and that there is a very clear zone of avoidance in the fractal range, i.e., for 1<D<2, with an actual gap in the benign histograms for the bin centered at D=1.5 for both views. For the malignant cases, it is the opposite: Euclidean zones are avoided and the data are very clearly centered in the fractal range for both views, with the peak of the histograms at D=1.5. A statistical comparison between benign vs. malignant MC clusters was performed using the Wilcoxon rank-sum test, which yielded p-values of 0.009 for CC comparisons and 0.014 for MLO comparisons for the benign vs. malignant fractal dimension distributions. These are statistically significant differences.

Example 6

The CC-MLO Fractal Dimension Plot and Fractal Zone

Figure 12:
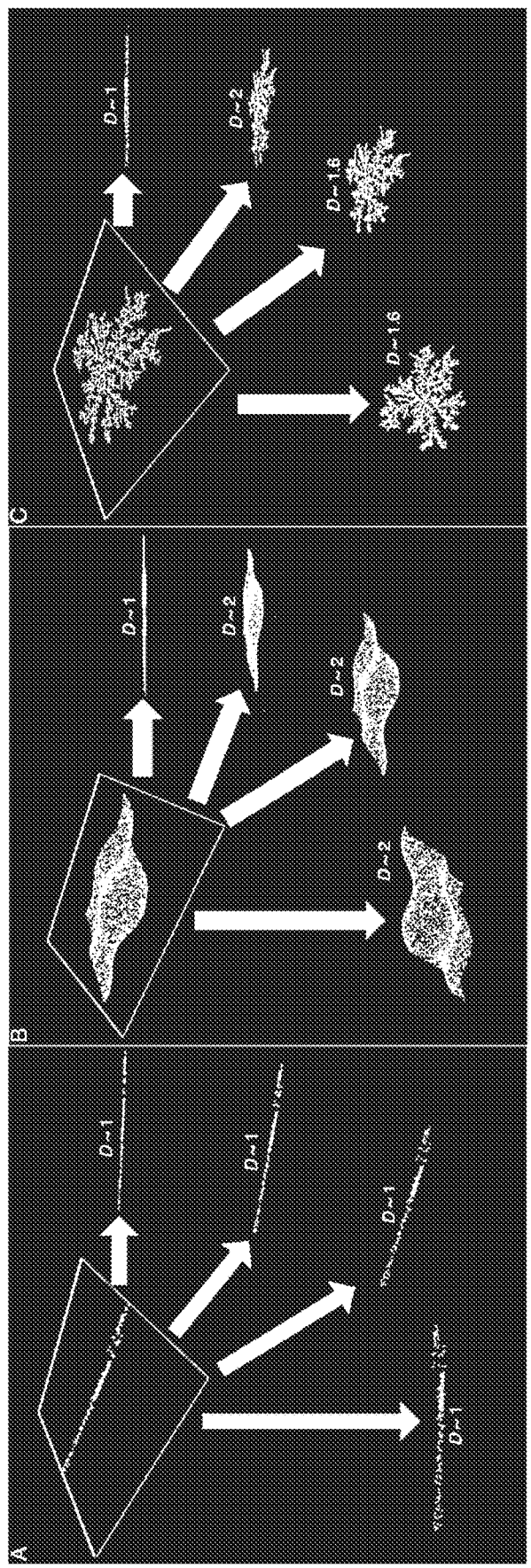
FIG. 12 shows exemplary random point distribution models to describe how different kinds of objects can have only a limited number of possible fractal dimension as a function of the projection angle; the left panel (12A) shows the possible fractal dimensions of a line; the center panel (12B) shows the possible fractal dimensions of a surface, and the right panel (12C) shows the possible fractal dimensions of a fractal cluster (here a simulated diffusion-limited aggregate).

In this Example, a fractal dimension plot between the MLO and CC views of a breast is calculated. Unless otherwise specified, all samples, sample handling, and analysis was as described above in Example 5. As shown in Example 5, the significance of the difference between benign and malignant is quite interesting. However, it is still only based on statistics of populations. The histograms in FIG. 10 show that, when each view is taken independently (CC or MLO), it is still possible, though unlikely, for a malignant lesion to have a Euclidean dimension, and vice-versa, for benign lesions to have a (non-integer) fractal dimension. However, in order to work towards a potential CAD method that would be able to diagnose breast lesions individually instead of via the population statistics, we combined the information to indirectly infer the 3D structure of the tumor embedded into the breast tissue. This is presented in a novel plot called the "CC-MLO fractal dimension plot" shown in FIG. 11, where red dots represent malignant cases and green dots represent benign cases. The square centered at (1.5, 1.5) represents those cases for which both CC and MLO views have a fractal dimension that is within 1.2<D<1.8. Note that only malignant cases are found in this internal square. However, having one of the two views with a score that is close to D=1.5 may "compensate" for its other view being outside of the [1.2, 1.8]×[1.2, 1.8] square, i.e., as one view approaches D=1.5, the farther from 1.5 the other can be. Further justification is presented below and in FIG. 12. That is how the triangular regions that decay linearly as a function of distance from the internal square were defined. Therefore, the central square, combined with the four triangular regions extending from it are what we define as the "fractal zone". Of the 59 cases considered in this study, 92% of malignant breast lesions studied (23 out of 25) were in the fractal zone while 88% of the benign lesions were in the Euclidean zones (30 out of 34).

Bayesian Analysis

The inferences from a Bayesian analysis are richer and more informative than null hypothesis significance testing. In particular, there is no reliance on p-values. But also, Bayesian models are designed to be appropriate to the data structure without having to make approximation assumptions typical in null hypothesis significance testing. The results reported above show that the vast majority of malignant breast lesions are fractal, and that the vast majority of benign breast lesions are Euclidean. However, the condition of interest is how breast lesions in the fractal zone can indicate malignancy, and how breast lesions in the Euclidean zone can indicate benignancy.

Bayesian inference derives the posterior probability as a consequence of two antecedents, a prior probability and a likelihood function derived from a probability model for the data to be observed. In this application, the model is based on historical radiology assessment scores using the BI-RADS system. A detailed description of this probability model as well as the mathematical model behind Bayes analysis is presented in the Methods section. Bayesian inference then becomes a computation of the posterior probability according to Bayes' rule. The interpretable output of this Bayesian analysis is the so-called 95% highest density interval (HDI), which is analogous to the 95% confidence interval in frequentist statistics. The 95% HDI from the resulting posterior distribution indicates that the percentage of breast lesions in the fractal zone that are malignant is between 74.2% and 97.5%. Alternatively, in terms of controlling for false positives, which is a major concern, as discussed in the Introduction, the percentage of breast lesions in the Euclidean zone that are benign is between 75.7% and 96.2%.

Interpretation of the 3D Geometrical Structure

Even though two different 2D views of a 3D object are insufficient to fully characterize its 3D geometry, it can nonetheless give a robust estimate, as shown in this Example. The cases outside of the fractal zone can be categorized in two Euclidean subsets: 1) LINES, i.e. those that are approximately in the ($D_{CC}$=1,$D_{MLO}$=1) area, which are therefore seen as one-dimensional objects from both views (FIG. 12A, left panel); or 2) SHEETS, i.e. those that are either in the ($D_{CC}$=1, $D_{DMLO}$=2) or ($D_{CC}$=2, $D_{MLO}$=1) areas, which are seen as a full two-dimensional object in one view, but as a one-dimensional object from the other view and also those that are in the ($D_{CC}$=2, $D_{MLO}$=2) area, which are seen as a full two-dimensional object from both views (FIG. 12B, center panel). Although simplistic, these case models represent a good estimate of what the 3D Euclidean structure of a benign lesion may look-like.

For the cases that fall in the fractal zone, those malignant lesions that are in the [1.2,1.8]×[1.2,1.8] square have a fractal signature that is seen from both views, whereas those that are in the triangular areas would represent fractal clusters that grow onto a 2D plane, i.e. seen as a fractal from one view, but seen either as a line (bottom or left triangular regions) or a plane (top or right triangular regions) from the other view (FIG. 12C, right panel). Interestingly, a diffusion-limited aggregate embedded in 3D space and for which 2<D<3 will have a 2D projection with D=2. Since no malignant lesions are found in the ($D_{CC}$=2, $D_{MLO}$=2) area of the CC-MLO fractal dimension plot, we can safely hypothesize that all tumors are essentially limited to a 2-dimensional fractal structure (within the 3-dimensional breast tissue), for which 1<D<2. Without wishing to be held to a particular theory, this therefore leads us to conjecture that all breast tumors considered in this study, benign and malignant, fractal or Euclidean, would grow on 2-dimensional manifolds.

Examples 5 and 6 illustrate embodiments of provided methodologies which offer a way to accurately classify benign and malignant tumors based on their invasiveness as determined by the geometrical structure. By considering the organization of tumors via CAD systems, current mammographic practice may be improved by increasing accuracy, and potentially decreasing recall rates and costs. The inferred 3-dimensional geometry of the breast lesions based on the analysis of the mammographic images using the 2D WTMM methodology allows one to explore the invasiveness of the breast tumors and provide an interpretation of the severity of the lesion. By considering where each case falls on the CC-MLO fractal dimension plot, a score similar to the Breast Imaging-Reporting and Data System (BI-RADS) assessment score may be assigned to each case. Not only does this tool have the potential as a CAD, but it may also provide insight into the underlying mechanisms that drive overall growth and structure at the time of the screening mammogram.

Without wishing to be held to a particular theory, it is contemplated that, since the structure of the tumors are different, with benign lesions likely being smooth Euclidean objects and malignant lesions being branching objects (and possibly, for both cases, being restricted to growing along 2D manifolds within the 3D breast tissue environment), there may be a link to the cellular mechanisms at the lower levels in the system that drive the organization at the much larger scale of mammograms. Use of provided methods may be helpful in revealing these relationships and improving detection and treatment.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:
1. A method comprising
providing a first view of a region of tissue;
providing a second view of the region of tissue;
calculating a first fractal dimension for the first view of the region of tissue; and
calculating a second fractal dimension for the second view of the region of tissue;
wherein a fractal zone is defined as a polygon consisting of a central square and a first, second, third, and fourth extending triangular region as plotted on a graph of the fractal dimension of the first view of the region of tissue by the fractal dimension of the second view of the region of tissue; and
wherein if the fractal dimension of at least one of the first fractal dimension and the second fractal dimension is in the fractal zone, the region of tissue is considered cancerous.

2. The method of claim 1, further comprising treating the region of tissue if it is cancerous.

3. The method of claim 1, wherein the central square and first, second, third and fourth extending triangular regions are defined by the following fractal dimensions, as plotted on a graph of the fractal dimension of the first view by the fractal dimension of the second view:
central square: (1.2, 1.2), (1.2, 1.8), (1.8, 1.2)(1.8, 1.8);
first extending triangular region: (0.5, 1.5), (1.2, 1.2), (1.2, 1.8);
second extending triangular region: (1.5, 0.5), (1.2, 1.2), (1.8, 1.2);
third extending triangular region: (1.5, 2.3), (1.2, 1.8), (1.8, 1.8); and
fourth extending triangular region: (2.3, 1.5), (1.8, 1.2), (1.8, 1.8).

4. The method of claim 1, wherein the central square and first, second, third and fourth extending triangular regions are defined by the following fractal dimensions, as plotted on a graph of the fractal dimension of the first view by the fractal dimension of the second view:
central square: (1.1, 1.1), (1.1, 1.9), (1.9, 1.1)(1.9, 1.9);
first extending triangular region: (0.5, 1.5), (1.1, 1.1), (1.1, 1.9);
second extending triangular region: (1.5, 0.5), (1.1, 1.1), (1.9, 1.1);
third extending triangular region: (1.5, 2.3), (1.1, 1.9), (1.9, 1.9); and
fourth extending triangular region: (2.3, 1.5), (1.9, 1.1), (1.9, 1.9).

5. The method of claim 1, wherein the central square and first, second, third and fourth extending triangular regions are defined by the following fractal dimensions, as plotted on a graph of the fractal dimension of the first view by the fractal dimension of the second view:
central square: (1.3, 1.3), (1.3, 1.7), (1.7, 1.3)(1.7, 1.7);
first extending triangular region: (0.5, 1.5), (1.3, 1.3), (1.3, 1.7);
second extending triangular region: (1.5, 0.5), (1.3, 1.3), (1.7, 1.3);
third extending triangular region: (1.5, 2.3), (1.3, 1.7), (1.7, 1.7); and
fourth extending triangular region: (2.3, 1.5), (1.7, 1.3), (1.7, 1.7).

6. The method of claim 1, further comprising
providing a third view of the region of tissue; and
calculating a third fractal dimension for the third view of the region of tissue;
wherein if the fractal dimension of at least one of the first fractal dimension, the second fractal dimension, and the third fractal dimension is in the fractal zone, the region of tissue is considered cancerous.

7. The method of claim 1, wherein the tissue is selected from breast tissue, brain tissue, lung tissue, kidney tissue, liver tissue, uterine tissue, dermal tissue, and pancreatic tissue.

8. An apparatus comprising:
a memory for storing a set of instructions; and
a processor for executing the set of instructions, wherein the instructions, when executed, cause the processor to:
provide a first view of a region of tissue;
provide a second view of the region of tissue;
calculate a first fractal dimension for the first view of the region of tissue; and
calculate a second fractal dimension for the second view of the region of tissue;
wherein a fractal zone is defined as a polygon consisting of a central square and a first, second, third, and fourth extending triangular region as plotted on a graph of the fractal dimension of the first view of the region of tissue by the fractal dimension of the second view of the region of tissue; and
determine if one or more of the fractal dimension and the second fractal dimension is in the fractal zone.

9. The apparatus of claim 8, wherein the central square and first, second, third and fourth extending triangular regions are defined by the following fractal dimensions, as plotted on a graph of the fractal dimension of the first view by the fractal dimension of the second view:
central square: (1.2, 1.2), (1.2, 1.8), (1.8, 1.2)(1.8, 1.8);
first extending triangular region: (0.5, 1.5), (1.2, 1.2), (1.2, 1.8);

second extending triangular region: (1.5, 0.5), (1.2, 1.2), (1.8, 1.2);

third extending triangular region: (1.5, 2.3), (1.2, 1.8), (1.8, 1.8); and fourth extending triangular region: (2.3, 1.5), (1.8, 1.2), (1.8, 1.8).

10. The apparatus of claim 8, wherein the central square and first, second, third and fourth extending triangular regions are defined by the following fractal dimensions, as plotted on a graph of the fractal dimension of the first view by the fractal dimension of the second view:

central square: (1.1, 1.1), (1.1, 1.9), (1.9, 1.1)(1.9, 1.9);

first extending triangular region: (0.5, 1.5), (1.1, 1.1), (1.1, 1.9);

second extending triangular region: (1.5, 0.5), (1.1, 1.1), (1.9, 1.1);

third extending triangular region: (1.5, 2.3), (1.1, 1.9), (1.9, 1.9); and fourth extending triangular region: (2.3, 1.5), (1.9, 1.1), (1.9, 1.9).

11. The apparatus of claim 8, wherein the central square and first, second, third and fourth extending triangular regions are defined by the following fractal dimensions, as plotted on a graph of the fractal dimension of the first view by the fractal dimension of the second view:

central square: (1.3, 1.3), (1.3, 1.7), (1.7, 1.3)(1.7, 1.7);

first extending triangular region: (0.5, 1.5), (1.3, 1.3), (1.3, 1.7);

second extending triangular region: (1.5, 0.5), (1.3, 1.3), (1.7, 1.3);

third extending triangular region: (1.5, 2.3), (1.3, 1.7), (1.7, 1.7); and fourth extending triangular region: (2.3, 1.5), (1.7, 1.3), (1.7, 1.7).

12. The apparatus of claim 8, wherein the processor further:

provides a third view of the region of tissue; and calculates a third fractal dimension for the third view of the region of tissue.

13. The apparatus of claim 8, wherein the tissue is selected from breast tissue, brain tissue, lung tissue, kidney tissue, liver tissue, uterine tissue, dermal tissue, and pancreatic tissue.

* * * * *